(12) United States Patent
Buck

(10) Patent No.: US 12,329,383 B2
(45) Date of Patent: *Jun. 17, 2025

(54) ANASTOMOTIC COUPLER

(71) Applicant: Buck Surgical, Inc., St. Louis, MO (US)

(72) Inventor: Donald W. Buck, St. Louis, MO (US)

(73) Assignee: Buck Surgical, Inc., St. Louis, MO (US)

( * ) Notice: Subject to any disclaimer, the term of this patent is extended or adjusted under 35 U.S.C. 154(b) by 804 days.

This patent is subject to a terminal disclaimer.

(21) Appl. No.: 17/536,439

(22) Filed: Nov. 29, 2021

(65) Prior Publication Data

US 2022/0079597 A1 Mar. 17, 2022

Related U.S. Application Data

(63) Continuation-in-part of application No. 17/365,484, filed on Jul. 1, 2021, which is a continuation-in-part of application No. 17/181,440, filed on Feb. 22, 2021, now Pat. No. 11,998,208, which is a continuation of application No. 16/950,209, filed on Nov. 17, 2020, now Pat. No. 10,939,913.

(60) Provisional application No. 63/061,303, filed on Aug. 5, 2020, provisional application No. 62/936,868, filed on Nov. 18, 2019.

(51) Int. Cl.
*A61B 17/11* (2006.01)

(52) U.S. Cl.
CPC ....... *A61B 17/11* (2013.01); *A61B 2017/1107* (2013.01); *A61B 17/1114* (2013.01); *A61B 2017/1132* (2013.01); *A61B 2017/1139* (2013.01)

(58) Field of Classification Search
CPC ............. A61B 17/11; A61B 17/1114; A61B 2017/1107; A61B 2017/1132; A61B 2017/1135
See application file for complete search history.

(56) References Cited

U.S. PATENT DOCUMENTS

| 3,316,914 | A | 5/1967 | Collito |
| 3,357,432 | A | 12/1967 | Sparks |
| 6,241,743 | B1 | 6/2001 | Levin et al. |
| 6,402,767 | B1 | 6/2002 | Nash et al. |
| 6,569,173 | B1 | 5/2003 | Blatter et al. |

(Continued)

FOREIGN PATENT DOCUMENTS

| CN | 103 750 875 A | 4/2014 |
| WO | 2009/118719 A1 | 10/2009 |
| WO | 2013/004263 A | 1/2013 |

OTHER PUBLICATIONS

European Search Report (EESR) of European Patent Application No. EP 20890827.7, dated Jul. 24, 2023.

(Continued)

*Primary Examiner* — Todd J Scherbel
(74) *Attorney, Agent, or Firm* — POLSINELLI PC

(57) ABSTRACT

An anastomotic coupler is provided. A ring can include a plurality of receiving portions. A fixation device includes a cartridge. The cartridge includes a plurality of fasteners. Upon actuation of the fixation device, the fasteners puncture the tubular structure. The fasteners are received by the receiving portions such that the tubular structure is coupled with the ring.

12 Claims, 22 Drawing Sheets

(56) References Cited

U.S. PATENT DOCUMENTS

| | | |
|---|---|---|
| 10,939,913 B1 | 3/2021 | Buck |
| 11,672,539 B2 | 6/2023 | Agarwal et al. |
| 11,998,208 B2 | 6/2024 | Buck |
| 2001/0039425 A1 | 11/2001 | Dakov |
| 2002/0082625 A1* | 6/2002 | Huxel .................. A61B 17/115 606/153 |
| 2004/0054405 A1 | 3/2004 | Richard et al. |
| 2006/0004394 A1 | 1/2006 | Amarant |
| 2008/0114385 A1 | 5/2008 | Byrum et al. |
| 2008/0200938 A1 | 8/2008 | Lui |
| 2011/0106118 A1 | 5/2011 | Son et al. |
| 2011/0270287 A1* | 11/2011 | Borghi .................. A61B 17/11 606/153 |
| 2011/0306994 A1 | 12/2011 | Bassan et al. |
| 2013/0110140 A1 | 2/2013 | Lin et al. |
| 2013/0193190 A1 | 8/2013 | Carter et al. |
| 2013/0267968 A1 | 10/2013 | Ferlin |
| 2019/0150928 A1 | 5/2019 | Boiman et al. |
| 2019/0175172 A1 | 6/2019 | Kollar et al. |
| 2019/0321046 A1 | 10/2019 | Williams |
| 2020/0113567 A1 | 4/2020 | Bakos et al. |
| 2020/0337707 A1 | 10/2020 | Ad-El et al. |
| 2023/0009775 A1 | 1/2023 | Buck |
| 2023/0240681 A1 | 8/2023 | Higdon et al. |

OTHER PUBLICATIONS

International Search Report (ISR) of PCT/US2024/050874, dated Dec. 12, 2024.
Vocabulary.com definition for "needle" accessed Oct. 20, 2023; (4 Pages) https://www.vocabulary.com/dictionary/needle.
Vocabular.com definition for "pin" accessed Oct. 20, 2023; (4 Pages) https://www.vocabulary.com/dictionary/pin.
Office Action for Chinese Application No. 202080069581.8, issued on May 8, 2023, 08 Pages (5 Pages of Official Copy and 3 Pages of English Translation).
Non-Final Office Action for U.S. Appl. No. 17/181,440, issued Oct. 26, 2023 (28 Pages).
International Search Report of PCT/US2020/060857 dated Jan. 18, 2021.
International Preliminary Report on Patentability of PCT/US20/60857 dated Feb. 9, 2021.
International Search Report (ISR) of PCT/US2024/053172, dated Jan. 8, 2024.
Office Action for U.S. Appl. No. 17/365,484, dated Jan. 21, 2025 (15 pages).

* cited by examiner

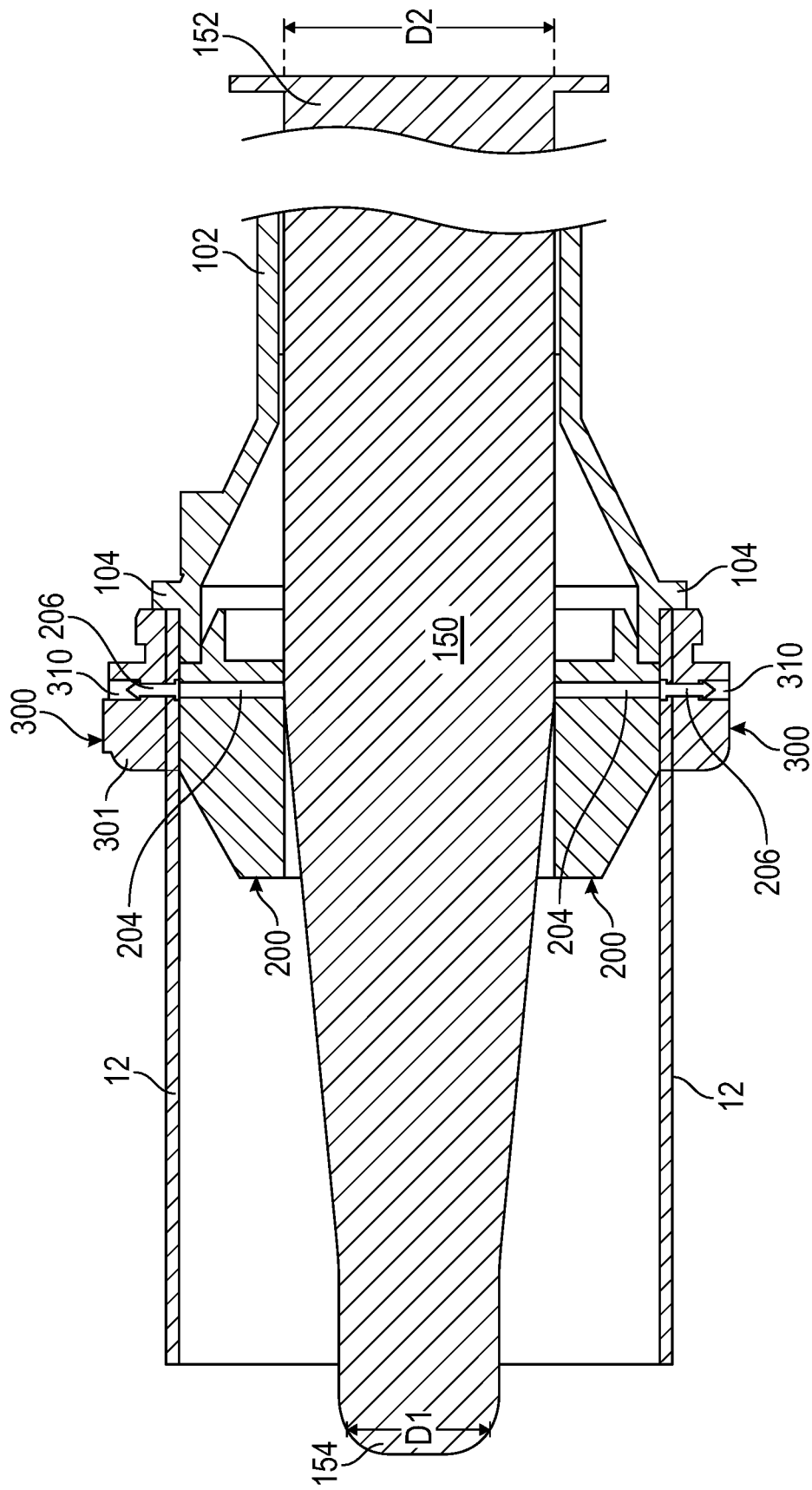

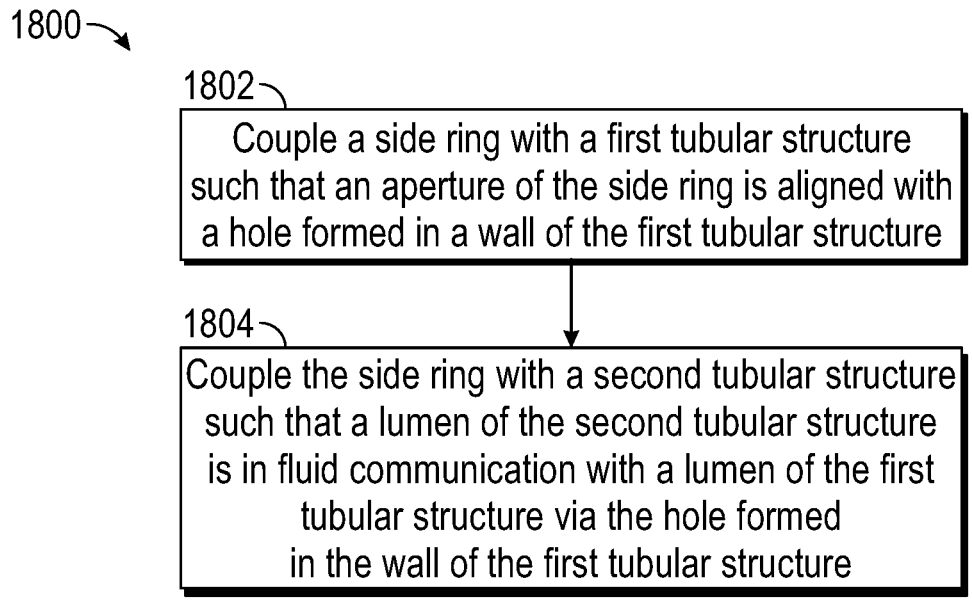
FIG. 18
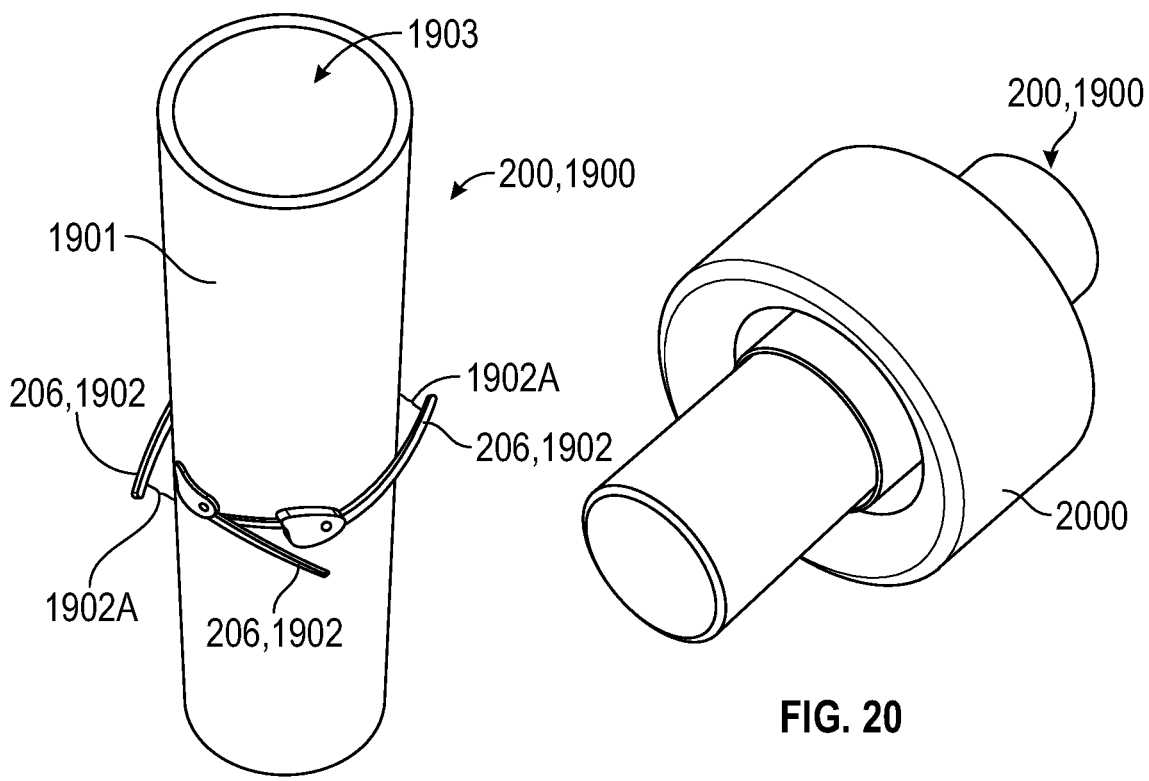
FIG. 19
FIG. 20

ANASTOMOTIC COUPLER

CROSS-REFERENCE TO RELATED APPLICATIONS

This application is a continuation-in-part application of U.S. application Ser. No. 17/365,484 filed Jul. 1, 2021, which is a continuation-in-part application of U.S. application Ser. No. 17/181,440 filed Feb. 22, 2021, which is a continuation application of U.S. application Ser. No. 16/950,209 filed Nov. 17, 2020, now U.S. Pat. No. 10,939,913, which claims the benefit of U.S. Provisional Patent Application No. 62/936,868, filed in the U.S. Patent and Trademark Office on Nov. 18, 2019, and U.S. Provisional Patent Application No. 63/061,303, filed in the U.S. Patent and Trademark Office on Aug. 5, 2020, each of which is incorporated herein by reference in its entirety for all purposes.

FIELD

The present disclosure relates generally to an anastomotic coupler. In at least one example, the present disclosure relates to a surgical system and method to utilize an anastomotic coupler to connect two tubular structures such as vessels, esophagus, intestine, lymphatic structure, and/or graft material.

BACKGROUND

An anastomosis is a connection between two luminal structures. Commonly, these connections can occur with blood vessels (for example, vascular anastomosis), or tubular gastrointestinal structures (for example, intestines, stomach, esophagus). Conventional techniques allow the anastomosis to be completed between two ends (referred to as end-to-end anastomosis), or between the end of one structure and the side of another structure (referred to as end-to-side anastomosis). Procedures requiring these anastomoses are carried out thousands of times per day, globally. Likewise, multiple surgical specialties rely upon the creation of reliable, unobstructed anastomoses for successful treatment of their respective patients.

BRIEF DESCRIPTION OF THE DRAWINGS

Implementations of the present technology will now be described, by way of example only, with reference to the attached figures, wherein:

FIG. 10A illustrates actuation of the fixation device;
FIG. 18 is a flow chart of a method for coupling an end of a tubular structure with a side of a tubular structure;
FIG. 19 illustrates an exemplary cartridge;
FIG. 20 illustrates the cartridge of FIG. 19 with a sheath covering the fasteners.

DETAILED DESCRIPTION

Figure 1:
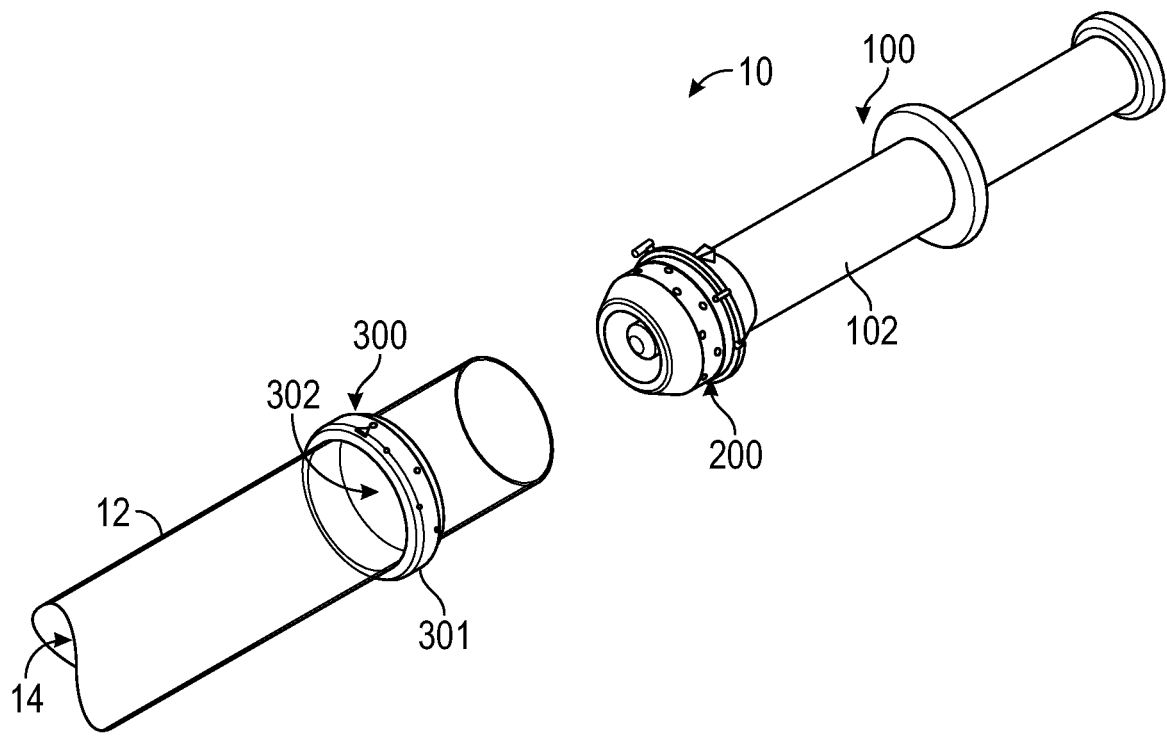
FIG. 1 illustrates a diagram of an anastomotic coupler.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the examples described herein. The drawings are not necessarily to scale and the proportions of certain parts may be exaggerated to better illustrate details and features of the present disclosure.

The original technique for vascular suture anastomoses was created by Alexis Carrel between 1901-1910. This pioneering work resulted in Carrel receiving the Nobel Prize in 1912. Despite 100 years of surgical evolution and innovation since that discovery, the majority of vascular anastomoses to this day still employ suture techniques similar to Carrel's initial description in the early 1900s. In the 1970s, gastrointestinal stapling devices were introduced, which quickly replaced primary suture techniques for bowel anastomoses. However, most surgeons still employ circumferential suture techniques in the serosal layer overlying the stapled anastomosis for added support. Although generally successful, these techniques can take long periods of time, often require additional surgical expertise, and if not performed correctly, may result in leakage (blood, stool contents, gastric contents, lymphatic fluid), constriction, stenosis, and/or obstruction at the anastomotic site. In the case of vascular anastomoses, stenosis and/or obstruction can result in catastrophic complications such as heart attack, stroke, peripheral limb ischemia, amputation, death, and reconstructive failure and soft-tissue loss. For example, in the setting of gastrointestinal anastomoses, these complications can result in extra-luminal leak of gastrointestinal contents, infection, sepsis, obstruction, and death.

With the understood importance of reliable, open anastomoses, alternatives to sutures and staples have been used. An example of a vascular anastomotic coupler is described, for instance, in U.S. Patent Pub. No. 2015/0088172 A1 (the '172 Publication). This coupler has two circular ends with spikes or pins. The vessel is brought through the ring and the vessel wall is everted, or rolled over, the pins for securement as shown in FIGS. 2A and 2B of the '172 Publication. This is completed on each vessel end, and the two rings are then brought together with the spikes/pins being forced into the opposite ring to join the ends together as shown in FIG. 1C of the '172 Publication. However, because of the potential for micro-motion of the vessels and size mismatch due to the anastomotic coupler of the '172 Publication, blood leakage may happen, and/or one of the pins may tear through the vessel wall creating a leak and/or site for platelet aggregation and thrombosis (blood clot formation). Likewise, with the anastomotic coupler of the '172 Publication, for thicker walled, less elastic vessels, particularly arteries, everting vessel edges can be quite difficult and may result in trauma to the vessel wall (intima) and/or stenosis at the anastomosis, both of which can create platelet aggregation, turbid flow, and/or thrombosis with subsequent obstruction of flow. Additionally, the technique of the '172 Publication requires additional specialized equipment (surgical microscope, high-powered loupe magnification) to use. For gastrointestinal stapled anastomoses, many procedures are performed either side-to-side which is not a natural pathway for intestinal smooth muscle propulsion of stool contents (for example, non-longitudinal flow along the length of the intestine), or end-to-end, which requires a separate, remote full-thickness bowel access incision for deployment, thereby creating a secondary weak point for potential leak, or adhesion formation.

Referring now to FIG. 1, an anastomotic coupler 10 is provided. The anastomotic coupler 10 is provided to create a connection between adjacent tubular structures 12. The tubular structure 12 can include blood vessels, grafts, prostheses, gastrointestinal structures, esophagus, lymphatics, and/or any other suitable channels of the body or the operation for which the tubular structure 12 is created. The tubular structure 12 forms a lumen 14 through which matter can be passed, for example blood, food, fluids, and/or cells.

The anastomotic coupler 10 includes a ring 300 forming an aperture 302. The ring 300 is operable to receive a tubular structure 12 through the aperture 302. While the ring 300 as illustrated in FIG. 1 has a substantially circular shape, the ring 300 can have any suitable shape such as rectangular, triangular, octagonal, hexagonal, and/or oval. Additionally, the ring 300 as illustrated in FIG. 1 is a singular solid piece, in some examples, for ease of application or manufacturing purposes, the ring 300 can include two semi-circular or arc-type pieces that are joined together around the tubular structure 12.

The size of the lumen 302 of the ring 300 can vary based on the application and the size of the tubular structure 12. For example, the diameter of the lumen 302 can range from about 0.5 millimeters (mm) (for example for lymphatic connections) to about 60 millimeters (for example for gastrointestinal connections). Due to the range of diameters for the ring 300, and the range of diameters for the tubular structure 12, the appropriate ring 300 can be selected by measuring the internal diameter of the tubular structure 12. This can be accomplished, for example, with an intraluminal measurement guide/device. If there is a significant size mismatch (1 mm or greater) between the tubular structure 12 and the ring 300, then a short, cylindrical tube connector with a corresponding male and female end can be used to allow for gradual transition in size in any direction to accommodate the size difference. For example, a cylindric tube can be provided that tapers in size such that one end is 1 mm-2 mm larger/smaller than the other end, which would enable a connection of a 1 mm vessel to a 2.5 mm-3.5 mm vessel during microsurgical procedures without problem and vice versa.

Figure 2:
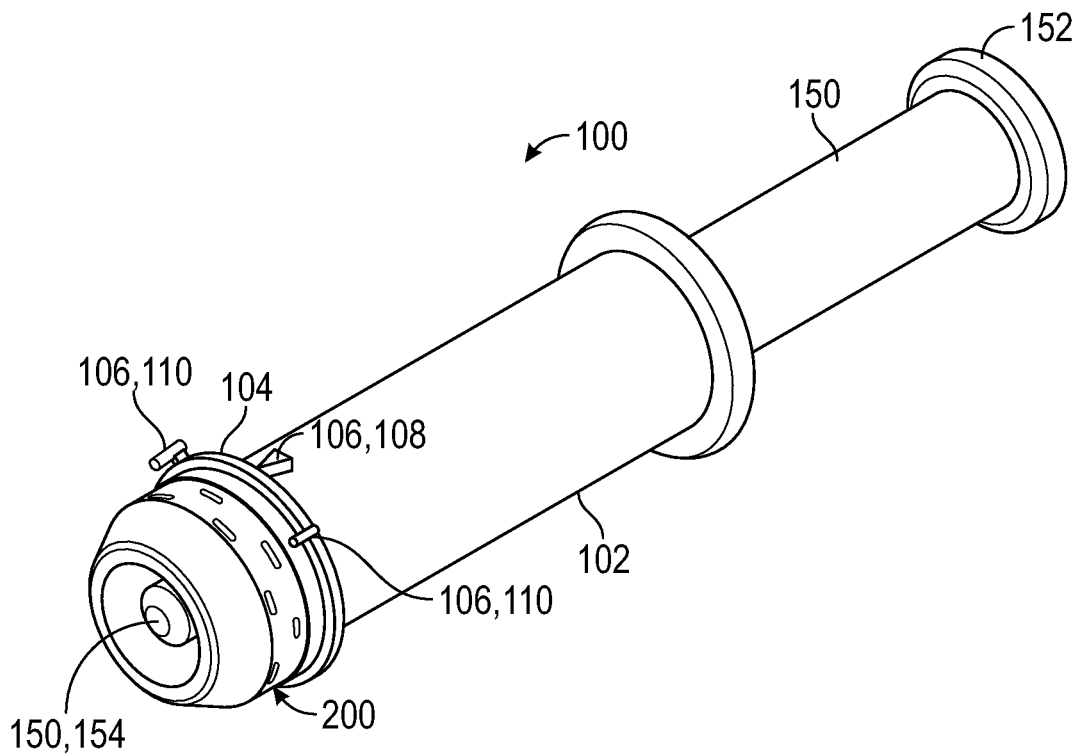
FIG. 2 illustrates a fixation device.

Referring also to FIG. 2, the anastomotic coupler 10 also includes a fixation device 100. The fixation device 100 is operable to couple the tubular structure 12 with the ring 300. The fixation device 100 can include a housing 102 and a cartridge 200. The cartridge 200 includes a plurality of fasteners 206 (as shown in FIGS. 5-10B). The fasteners 206 are operable to puncture the tubular structure 12 and be partially received in the ring 300 to couple the tubular structure 12 with the ring 300. In at least one example, the cartridge 200 can be removably coupled with the housing 102. Accordingly, the cartridge 200 may be replaceable to allow multiple uses of the fixation device 100. In some examples, the cartridge 200 may not be removable such that the fixation device 100 is provided for a one-time use. The fixation device 100 can include a pusher rod 150 operable to actuate the fixation device 100 to drive the fasteners 206 from the cartridge 200. Upon actuation of the fixation device 100, the pusher rod 150 can translate along a longitudinal axis.

Figure 3:
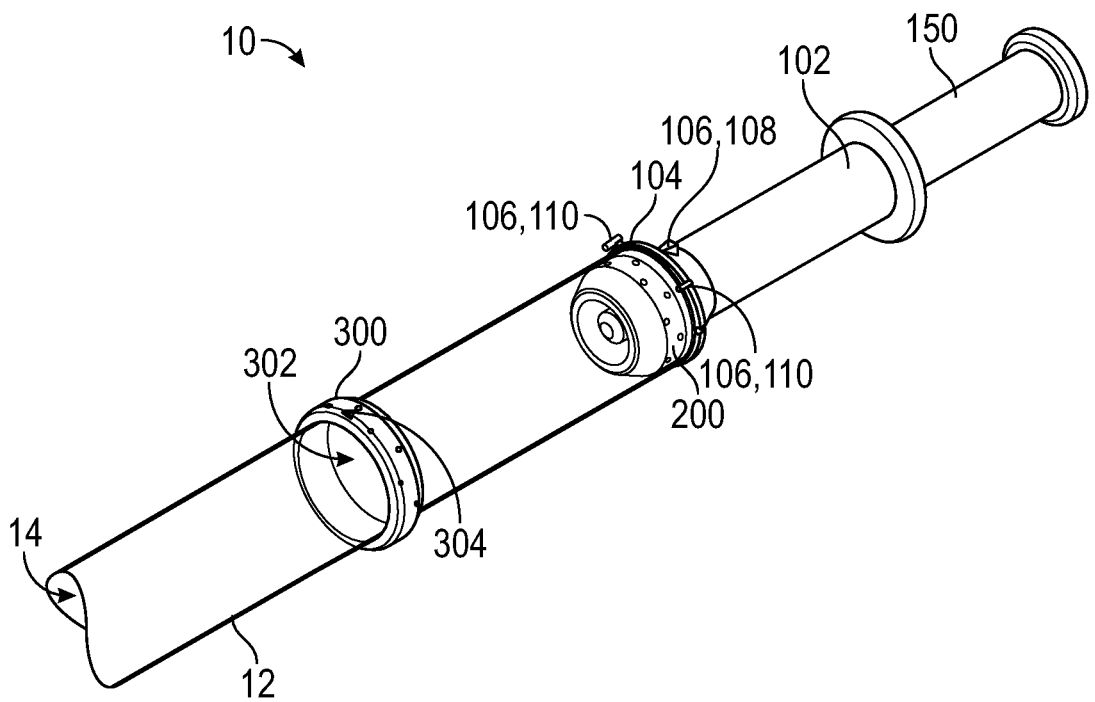
FIG. 3 illustrates a tubular structure being received by a fixation device.

The fixation device 100 includes stop 104 to receive the tubular structure 12. In at least one example, the stop 104 can be formed as a portion of the cartridge 200 to ensure alignment with the cartridge 200. In some examples, the stop 104 can be formed as a portion of the housing 102. The stop 104 extends radially from the housing 104 such that a free end of the tubular structure abuts the stop 104. As illustrated in FIG. 3, the housing 102 receives the free end of the tubular structure 12 such that the cartridge 200 is inserted into the lumen 14 of the tubular structure. When correctly positioned, the free end of the tubular structure 12 abuts the stop 104. The stop 104 ensures the placement and alignment of the ring 300, the cartridge 200, and the free end of the tubular structure 12. The alignment of the ring 300, the cartridge 200, and the free end of the tubular structure 12 is critical to ensure adequate connection between the tubular structure 12 and another tubular structure 12.

Figure 4:
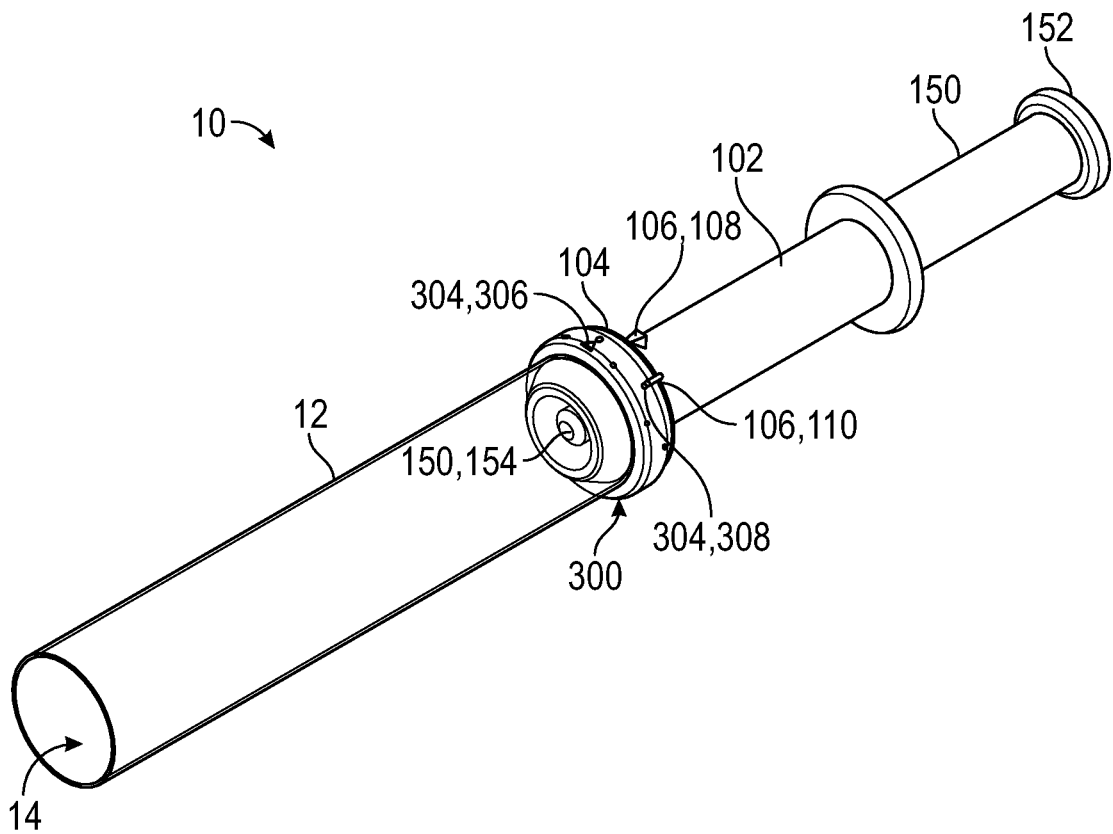
FIG. 4 illustrates a ring being aligned with a cartridge of the fixation device.

As illustrated in FIG. 4, after the tubular structure 12 is received by the fixation device 100 and abuts the stop 104, the ring 300 can be positioned to abut the stop such that the ring 300 is aligned with the free end of the tubular structure 12.

The stop 104 can include a plurality of alignment components 106 which correspond with alignment components 304 of the ring 300. Accordingly, when the ring 300 is aligned and/or correctly positioned, the alignment components 106 of the stop 104 are aligned with the alignment components 304 of the ring 300. In some examples, the alignment components 106, 304 can include one or more alignment markers 108, 304. The alignment markers 108, 304 can be shaped, for example as triangles. Accordingly, to align the ring 300, the tips of the triangles for the alignment markers 108, 304 can point towards one another. In some examples, the alignment components 106, 304 can include one or more alignment pins 110 and corresponding alignment receivers 308. When the ring 300 is aligned, the alignment pins 100 can be received by the alignment receivers 308. While the figures illustrate the alignment pins 100 being disposed on the fixation device 100 and the alignment receivers 308 being disposed on the ring 300, in some examples, the alignment pins 100 may be disposed on the ring 300 and the alignment receivers can be disposed on the fixation device 100.

Figure 5:
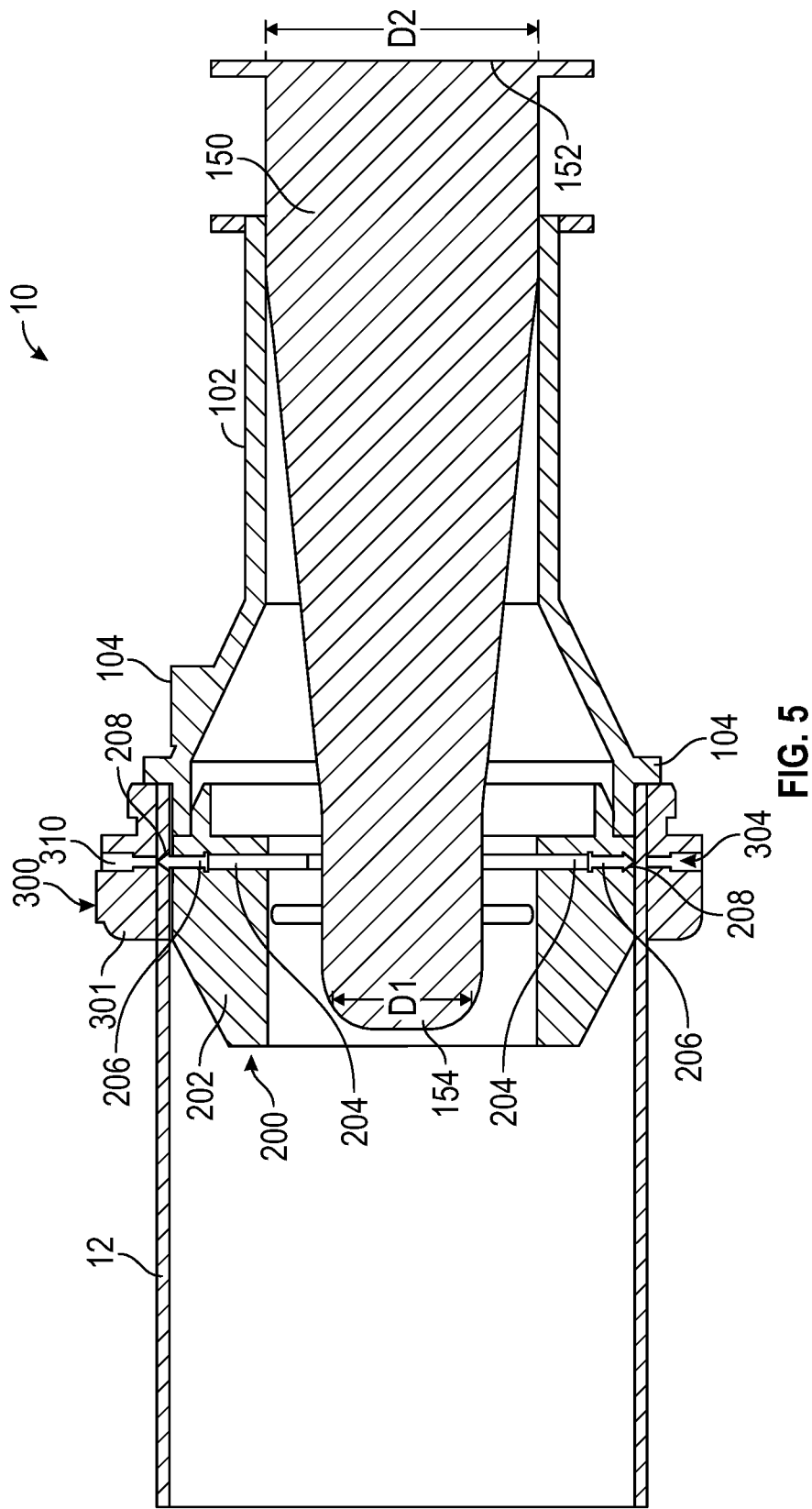
FIG. 5 illustrates a cross-sectional view of FIG. 4.

FIG. 5 illustrates a cross-sectional view of the tubular structure 12, the ring 300, and the cartridge 200 aligned. In addition to ensuring the ring 300 aligns with the free end of the tubular structure 12, the ring 300 is aligned with the cartridge 200. When the ring 300 is properly aligned with the cartridge 200, a plurality of receiving portions 310 of the ring 300 are aligned with the plurality of fasteners 206 of the cartridge 200.

The fasteners 206 can be any suitable fastener 206 to couple the ring 300 with the tubular structure 12 and prevent movement between the ring 300 and the tubular structure 12. For example, the fasteners 206 can include tacks 600, 700 (as shown in FIGS. 6 and 7), staples 800 (as shown in FIG. 8), pins, adhesive, internal ring, internal mesh, wire, clamp, coil, stent, and/or suture.

Figure 6:
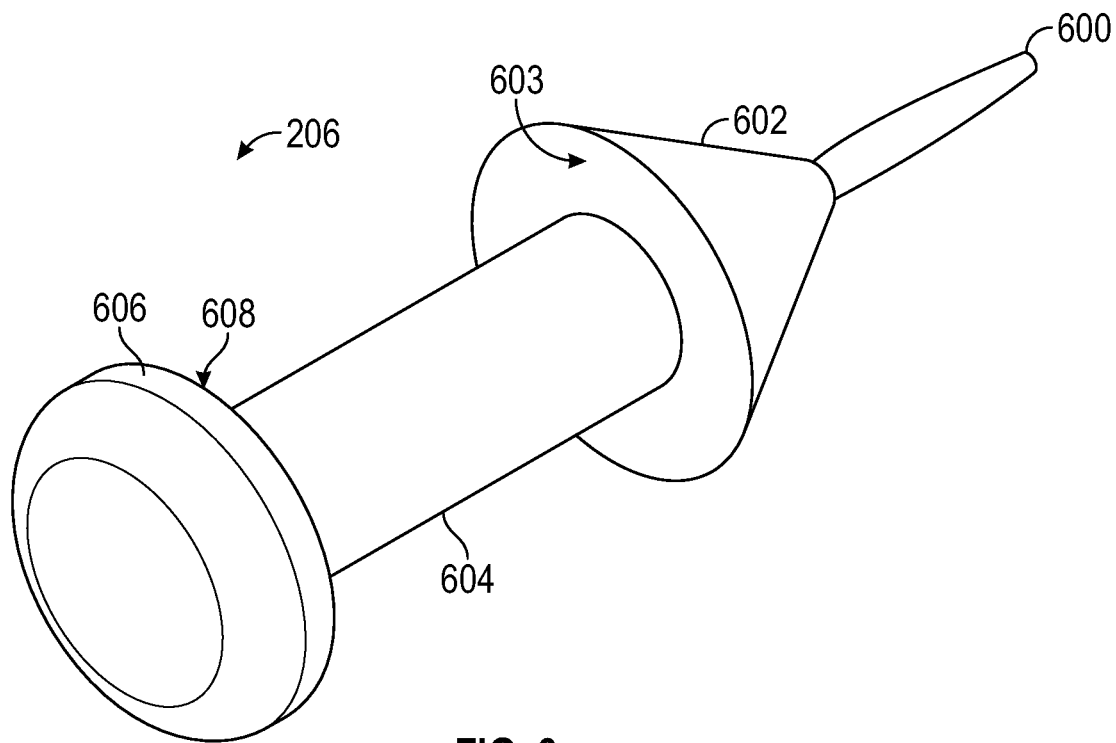
FIG. 6 illustrates an exemplary fastener.

As illustrated in FIG. 6, the tack 600 can include a puncturing portion 602 which is operable to puncture the tubular structure 12. An abutment surface 603 abuts against a surface of the corresponding receiving portion 310 of the ring 300. A body 604 spans the thickness of the wall of the tubular structure 12, and an end 606 includes an abutment surface 608 which abuts against the inner surface of the tubular structure 12. The abutment surfaces 603, 608 prevent the fastener 206 from being removed from the tubular structure 12 and the ring 300.

Figure 7:
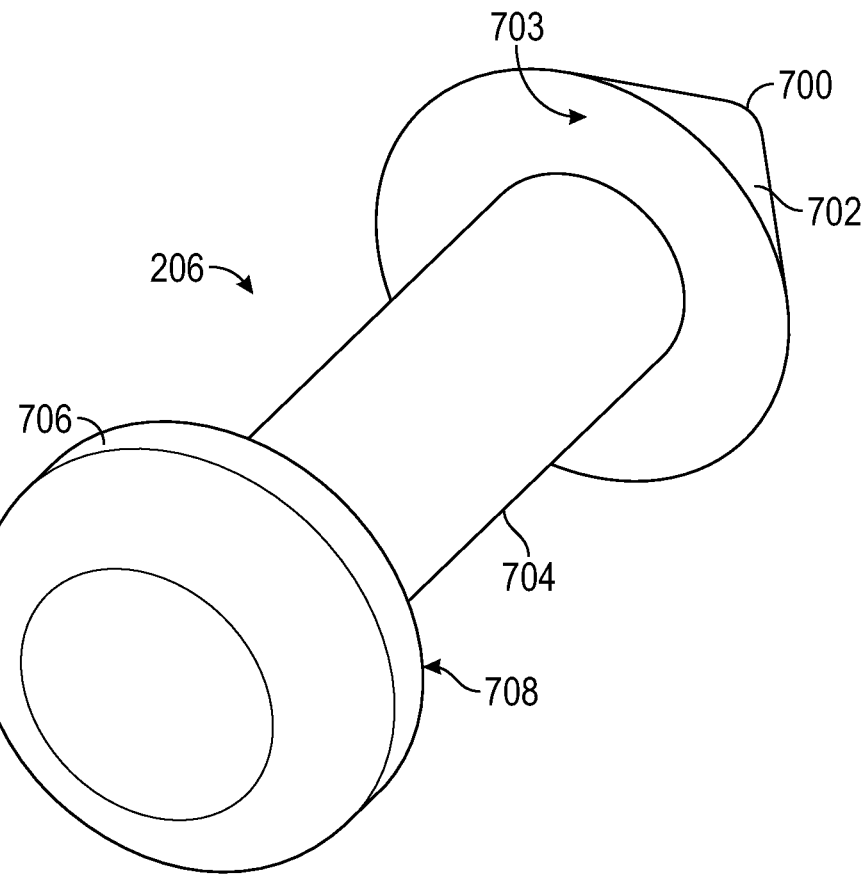
FIG. 7 illustrates another example of a fastener.

As illustrated in FIG. 7, the tack 700 can include a puncturing portion 702 which is operable to puncture the tubular structure 12. The exemplary tack 700 does not include as long of a puncturing portion 702 as the puncturing portion 602 as illustrated in FIG. 6. An abutment surface 703 abuts against a surface of the corresponding receiving portion 310 of the ring 300. A body 704 spans the thickness of the wall of the tubular structure 12, and an end 706 includes an abutment surface 708 which abuts against the inner surface of the tubular structure 12. The abutment surfaces 703, 708 prevent the fastener 206 from being removed from the tubular structure 12 and the ring 300.

Figure 8:
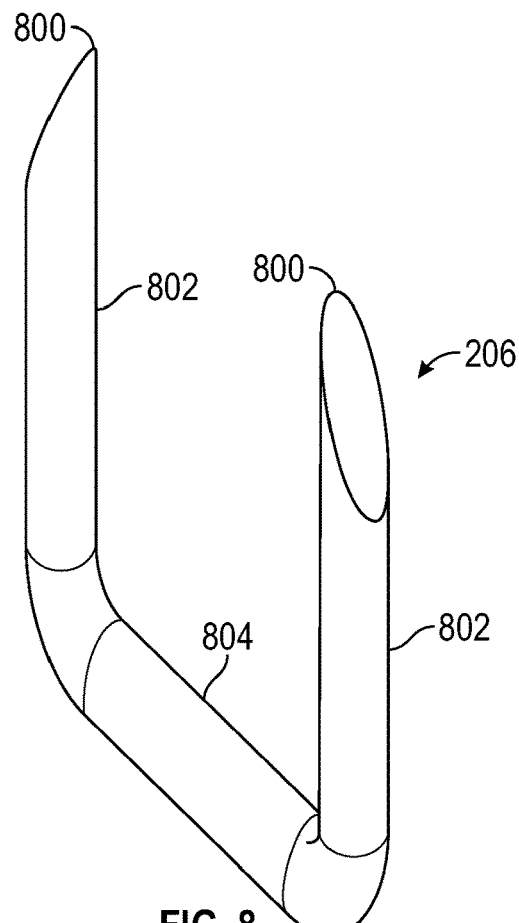
FIG. 8 illustrates another example of a fastener.

As illustrated in FIG. 8, the staple 800 can include two puncturing portions 802 which are operable to puncture through the tubular structure 12 and be received in the corresponding receiving portion 310 of the ring 300. A body 804 spans between the puncturing portions 802 and is operable to abut the inner surface of the tubular structure 12 to prevent the fastener 206 from being removed from the tubular structure 12. In at least one example, the puncturing portions 802 may be operable to bend or deform when received in the receiving portion 310 to prevent the puncturing portions 802 from being removed from the ring 300, ensuring coupling of the tubular structure 12 with the ring 300.

Figure 9:
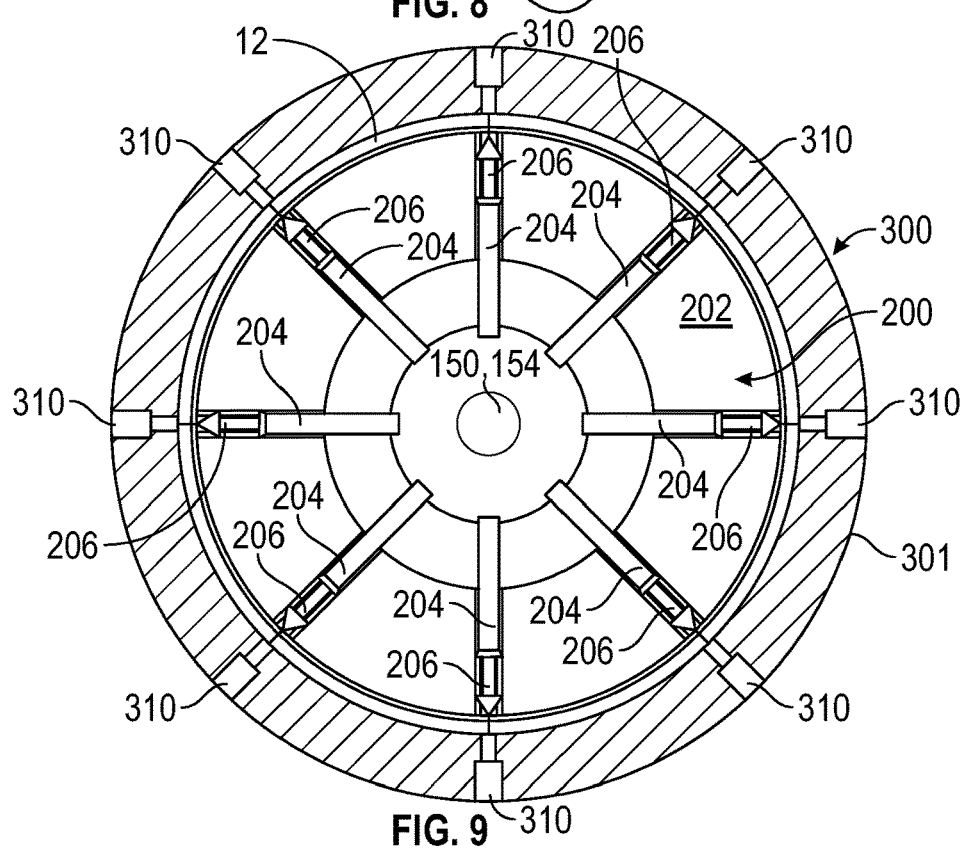
FIG. 9 illustrates a cross-sectional view of the cartridge aligned with the ring.

Referring to FIGS. 5 and 9, the cartridge 200 can include a plurality of drivers 204 corresponding with the plurality of fasteners 206. Upon actuation of the fixation device 100, the drivers 204 activate to push the corresponding fasteners 206 radially outward from the cartridge 200. The drivers 204 may include rods which abut the fasteners 206 and towards the center of the body 202 of the cartridge 200. In some examples, the drivers 204 may be spring loaded.

The pusher rod 150, as illustrated in FIG. 5, is tapered from a front portion 154 with a smaller diameter D1 to a rear portion 152 with a larger diameter D2 which is greater than the smaller diameter D1. The drivers 204 may abut the fasteners 206 on one end while extending into the cartridge 200 so that the opposing end of the fasteners 206 abut the pusher rod 150.

Figure 10B:
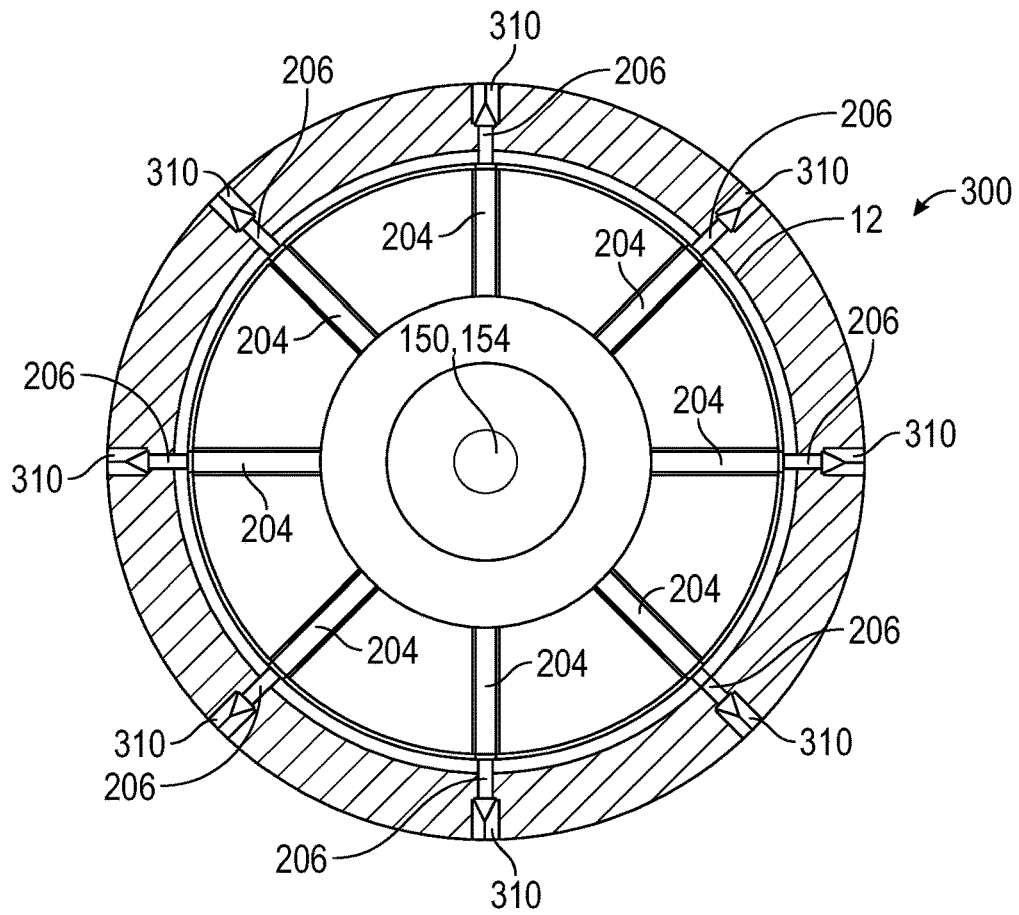
FIG. 10B illustrates a cross-sectional view of FIG. 10A.

Referring to FIGS. 10A and 10B, the fixation device 100 is actuated. Actuation of the fixation device 100 can include translating the pusher rod 150 along the longitudinal axis through the cartridge 200 from the front portion 154 towards the rear portion 152. The pusher rod 150, increasing in thickness, then activates the drivers 204 to drive the fasteners 206 radially outward from the cartridge 200, through the tubular structure 12, and into the receiving portions 310 of the ring 300. Once the ring 300 is coupled with the tubular structure 12, the fixation device 100 can be removed from the tubular structure 12. The ring 300 is then affixed or secured to the end of the tubular structure 12, maintaining the structure of the lumen of the tubular structure 12.

The fixation device 100, the ring 300, and/or the fasteners 206 can be made from mechanically suitable materials that are approved, and have sufficient strength, for use in the human or animal body. For example, the following materials, alone or in any combination, can be used: metals, in particular titanium or stainless steel, including the special alloys used for implants and medical instruments, nitinol, carbon materials, including carbon fiber meshes, soft plastic, for example silicone, hard plastic, for example Teflon, ceramic material, and/or bioresorbable material. The fixation device 100, the ring 300, and/or the fasteners 206 can be provided entirely or partially with a coating and/or structure that prevents or at least reduces the adherence of blood constituents. Such a coating can be composed of a material that smooths the surface. In at least one example, the coating can also contain anti-thrombotic medicaments (e.g. heparin).

Figure 11:
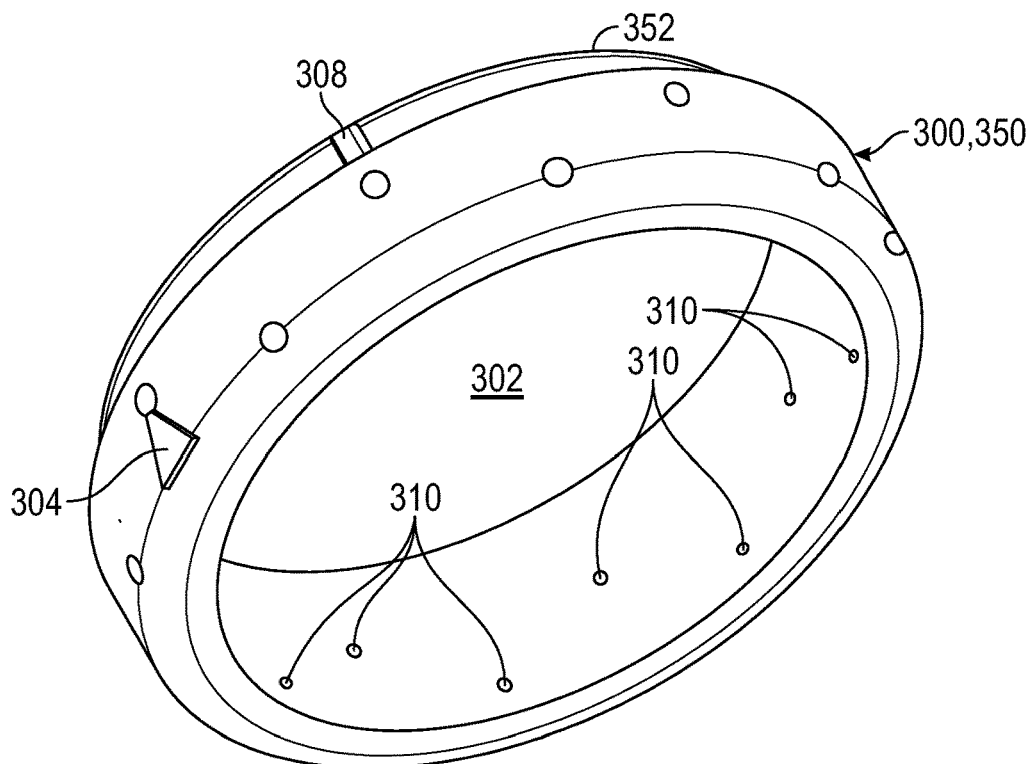
FIG. 11 illustrates an exemplary ring.
Figure 12:
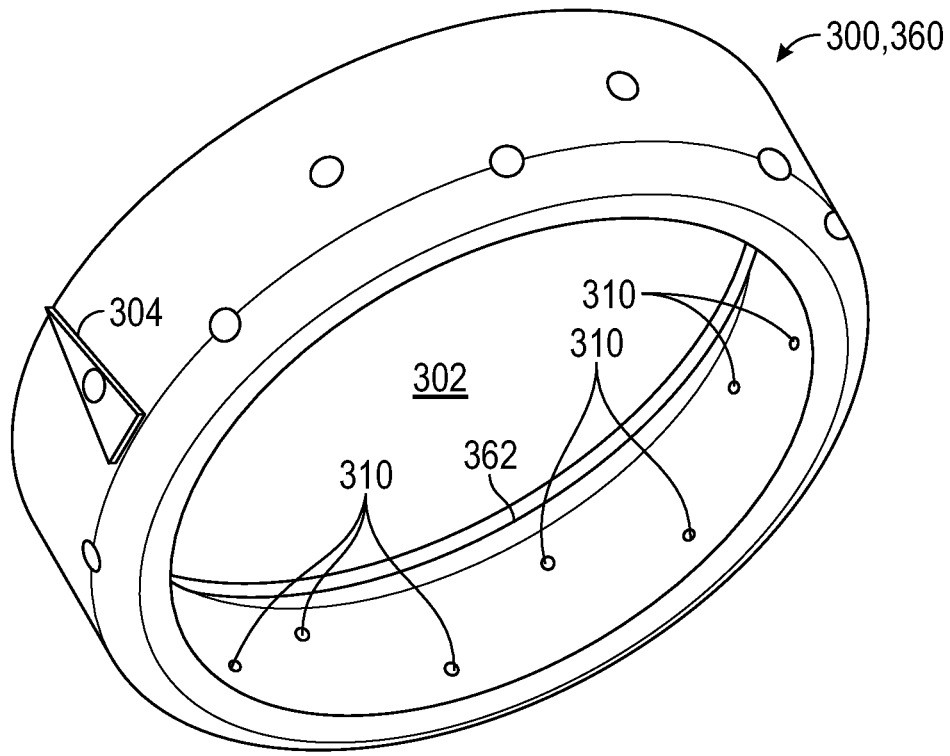
FIG. 12 illustrates an example of another ring.

The above process of coupling the ring 300 with the tubular structure 12 can be repeated for a second tubular structure 12 with a second ring 300. For example, FIG. 11 illustrates an exemplary male ring 350, and FIG. 12 illustrates an exemplary corresponding female ring 350. Similar to the ring 300 discussed above, the male ring 350 and the female ring 360 each include an aperture 302 operable to receive a tubular structure 12, receiving portions 310 operable to receive the fasteners 206, and alignment portions 304, 308. The male ring 350 includes a mating portion 352, and the female ring 360 includes a corresponding mating portion 362. The mating portion 352 is operable to couple with the mating portion 362 to couple the male ring 350 and the female ring 360 with one another. As illustrated in FIGS. 11 and 12, the mating portion 352 of the male ring 350 extends from the ring 350 and is operable to be received by the mating portion 362 of the female ring 360. In some examples, the rings 300 can be coupled with one another by, for example, fastening, snapping, clamping, stenting, tacking, pinning, loop and hook, adhesive, and/or other connecting method so long as the rings 300 are securely coupled with one another.

Figure 13:
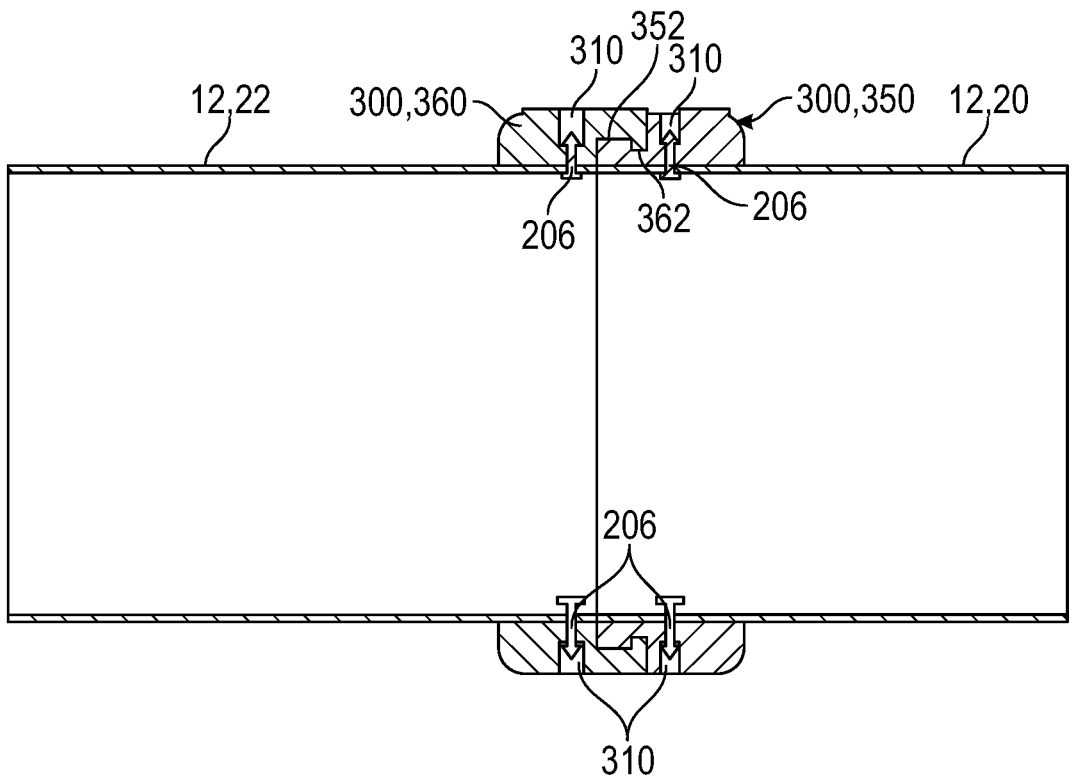
FIG. 13 illustrates a cross-sectional view of two rings coupled with one another to join two tubular structures.

As illustrated in FIG. 13, when the rings 350, 360 are coupled with one another, the lumens 14 of the two tubular structures 20, 22 are aligned in fluid communication with one another. In at least one example, the rings 350, 360 can create a seal to prevent fluid leakage. Accordingly, the anastomotic coupler 10 provides a more reliable, faster, more secure anastomotic coupling device to create a sealed, leak-proof, open connection between the ends of the tubular structures 20, 22 and allow for "stented" unobstructed flow of luminal contents through the connection/anastomosis (e.g. blood, lymph, fluid, stool contents, gastric contents, etc.). This connection can be strong enough to withstand tension, traction, and high flow pressure, which may occur with distal obstruction.

Figure 14:
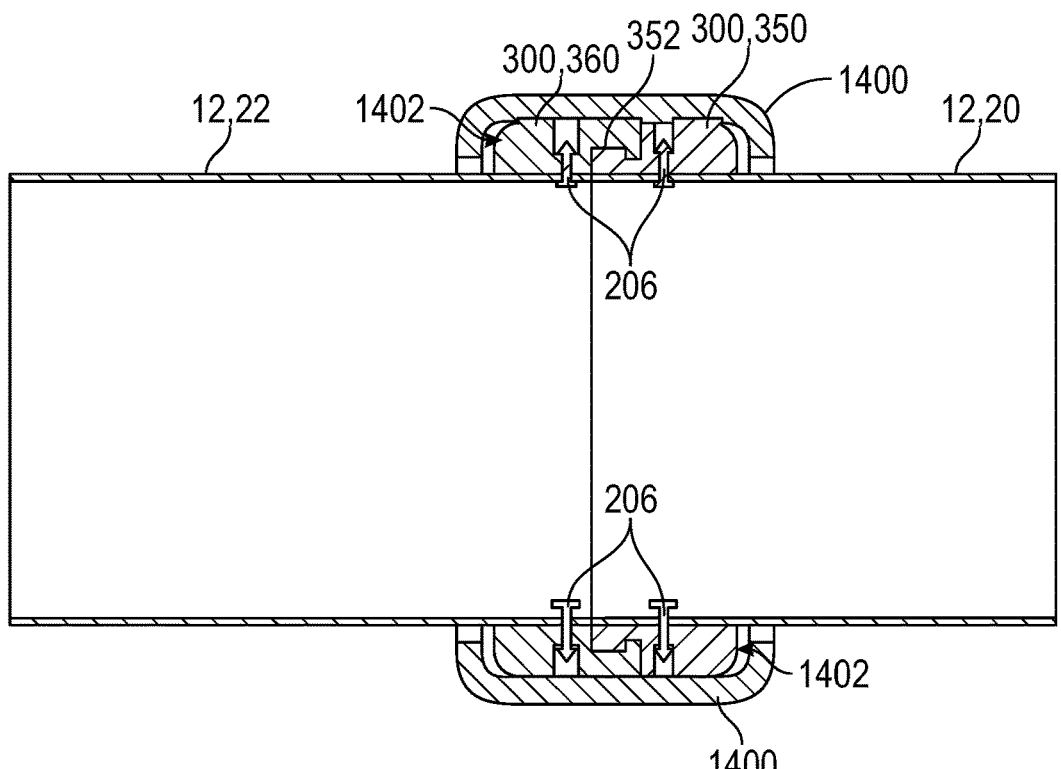
FIG. 14 illustrates a cap disposed over the two rings of FIG. 13.
Figure 15:
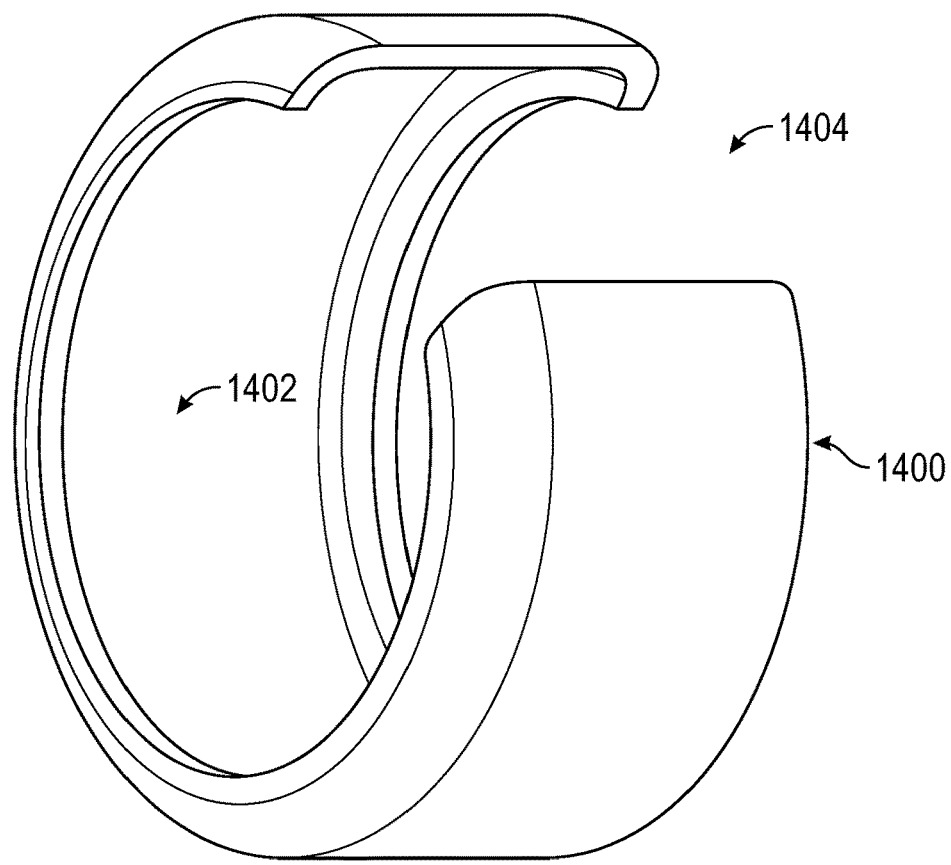
FIG. 15 illustrates an exemplary cap.

As illustrated in FIG. 14, a cap 1400 can be provided over the two rings 350, 360. The cap 1400 can assist in ensuring the connection between the rings 350, 360, as well as protecting the rings 350, 360 from external damage. As illustrated in FIG. 15, the cap 1400 can include a recess 1402 which is operable to receive the two rings 350, 360. An opening 1404 can be formed such that the cap 1400 can be deformed to snap over the two rings 350, 360.

Figure 16:
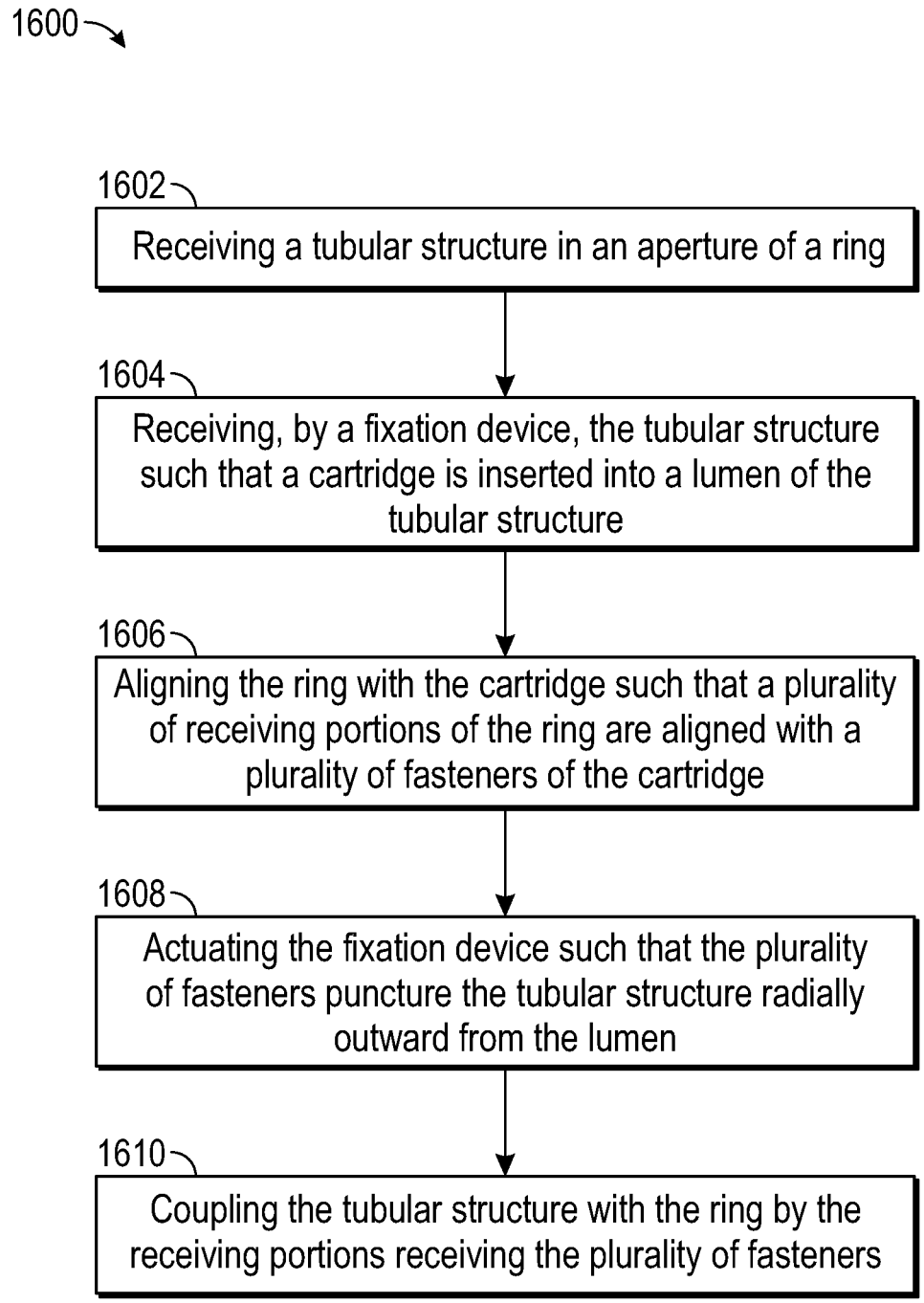
FIG. 16 is a flow chart of a method for utilizing an anastomotic coupler.

Referring to FIG. 16, a flowchart is presented in accordance with an example embodiment. The method 1600 is provided by way of example, as there are a variety of ways to carry out the method. The method 1600 described below can be carried out using the configurations illustrated in FIG. 1-15, for example, and various elements of these figures are referenced in explaining example method 1600. Each block shown in FIG. 16 represents one or more processes, methods or subroutines, carried out in the example method 600. Furthermore, the illustrated order of blocks is illustrative only and the order of the blocks can change according to the present disclosure. Additional blocks may be added or fewer blocks may be utilized, without departing from this disclosure. The example method 1600 can begin at block 1602.

At block 1602, a first tubular structure is received in an aperture of a first ring.

At block 1604, a fixation device receives the first tubular structure such that a first cartridge is inserted into a lumen of the first tubular structure.

At block 1606, the first ring is aligned with the first cartridge such that a plurality of receiving portions of the first ring are aligned with a plurality of fasteners of the first cartridge.

At block 1608, the fixation device is actuated such that the plurality of fasteners puncture the first tubular structure radially outward from the lumen. The cartridge can include a plurality of drivers corresponding with the plurality of fasteners. Upon actuation of the fixation device, the drivers activate to push the corresponding fasteners radially outward from the cartridge. In at least one example, the fixation device can include a pusher rod. The pusher rod can be tapered from a front portion with a smaller diameter to rear portion with a larger diameter. Upon actuation of the fixation device, the pusher rod can translate along a longitudinal axis to activate the drivers. In at least one example, to activate the drivers, the pusher rod translates along the longitudinal axis and passes through the cartridge from the front portion to the rear portion such that the pusher rod abuts and pushes the drivers and the corresponding fasteners radially outward from the cartridge.

At block 1610, the first tubular structure is coupled with the first ring by the receiving portions receiving the plurality of fasteners.

In at least one example, a second tubular structure can be received in an aperture of a second ring. A fixation device can receive the second tubular structure such that a second cartridge is inserted into a lumen of the second tubular structure. In at least one example, the fixation device may be the same fixation device that was utilized for the first ring. In some examples, the fixation device may be the same fixation device utilized for the first ring with a second cartridge that replaced the first cartridge. In some examples, the fixation device may be a second fixation device. The second ring can be aligned with the second cartridge such that a plurality of receiving portions of the second ring are aligned with a plurality of fasteners of the second cartridge. The fixation device can be actuated such that the plurality of fasteners puncture the second tubular structure radially outward from the lumen. The second tubular structure can be coupled with the second ring by the receiving portions receiving the plurality of fasteners.

The first ring can be aligned with the second ring such that the lumen of the first tubular structure and the lumen of the second tubular structure are aligned in fluid communication with one another. The first ring can be coupled with the second ring to join the first tubular structure with the second tubular structure, providing a continuous passage between the first tubular structure and the second tubular structure. In at least one example, a cap can be positioned about the first and the second ring to ensure the connection between the first ring and the second ring.

Figure 17A:
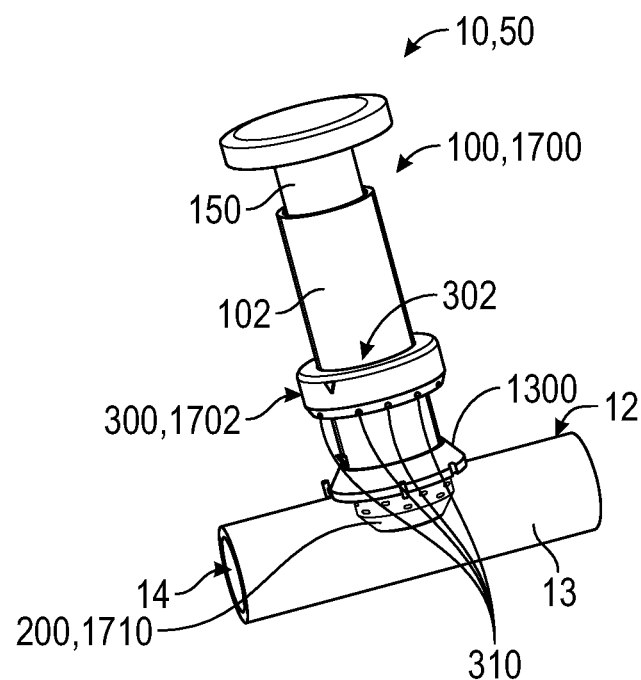
FIG. 17A illustrates a fixation device engaging with a side hole of a tubular structure.

FIGS. 17A-17E illustrate examples of an anastomotic coupler 10 which is operable to couple an end of a tubular structure 12 with a side of a tubular structure 12. Elements described in the system of FIGS. 17A-18 that have similar or the same name and/or the same reference numbers as elements in the disclosure for FIGS. 1-16 may have the same features as discussed above. While the discussion below for FIGS. 17A-17E may highlight some differences in features, the disclosure for the system of FIGS. 17A-18 are not limited to those and may also include any and/or all of the features as discussed above.

FIG. 17A illustrates alignment and positioning of a fixation device 100 and a ring 300 on a tubular structure 12. The fixation device 100 and the ring 300 are positioned such that the ring 300 can be coupled to the tubular structure 12 where an aperture 302 of the ring 300 can be aligned with a hole 1300 formed in a wall 13 of the tubular structure 12. In other words, the tubular structure 12 has a hole 1300 formed in a side wall 13. In at least one example, a cutting mechanism (not shown) can be operable to cut the hole 1300 in the wall 13 of the tubular structure 12. In some examples, the cutting mechanism can be a separate component operable to cut a precise hole 1300 in the wall 13 of the tubular structure 12. In some examples, the cutting mechanism can be part of the fixation device 1700 such that only one component is needed in the fixation device 1700 to cut a hole 1300 and couple the ring 300 to the tubular structure 12. The cutting mechanism can create a symmetrical, controllable-sized opening in the side wall 13 of the tubular structure 12.

In at least one example, the fixation device 1700 can be similar to fixation device 100 as discussed herein. In some examples, fixation device 1700 may be modified to couple the ring 1702 to the wall 13 of the tubular structure 12 to align with the hole 1300 in the wall 13 instead of coupling the ring 1702 to the tubular structure 12 in line with the lumen 14 of the tubular structure. In at least one example, the fixation device 1700 can include a stop which extends radially from the housing 102 such that the wall 13 of the tubular structure 12 abuts the stop. Accordingly, the fixation device 1700 provides guidance to the user for when the fixation device 1700 is in a desired position. In some examples, the stop can include a plurality of alignment components corresponding with alignment components of the ring 1702. As such, when the ring 1702 is aligned, the alignment components of the stop are aligned with the alignment components of the ring 1702.

Figure 17B:
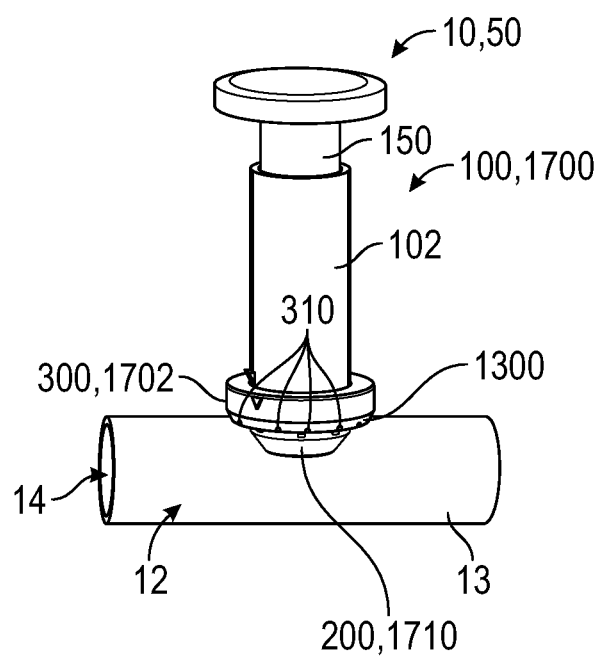
FIG. 17B illustrates a ring being aligned on the tubular structure of FIG. 17A.

As illustrated in FIGS. 17A and 17B, a cartridge 1710 can be disposed within the lumen 14 of the tubular structure 12. The cartridge 1710, similar to cartridge 300, includes a plurality of fasteners 260 (for example shown in 17C-17E)

operable to be received in corresponding plurality of receiving portions 310 in the ring 300. The ring 1702, as illustrated in FIGS. 17A-17E has a cylindrical shape. However, in other examples, the ring 1702 can have any suitable shape such that the ring 1702 can be aligned with the hole 1300 and prevent leakage between the tubular structure 12 and the ring 1702. The ring 1702, in some examples, may include a sealing component operable to abut against the wall 13 of the tubular structure 12 to prevent leakage of fluid.

In some examples, the position of the receiving portions 310 in the ring 1702 may be adjusted to better receive the plurality of fasteners 260 and provide a stronger coupling between the ring 1702 and the tubular structure 12. For example, as illustrated in FIGS. 17A-17E, the receiving portions 310 may be disposed towards the bottom of the ring 1702 so that the receiving portions 310 are adjacent to the tubular structure 12.

Similarly, in some examples, the position of the fasteners 260 in the cartridge 1710 may be adjusted towards the top to be adjacent to the wall 13 of the tubular structure 12. Accordingly, the distance between the fasteners 260 in the cartridge 1710 and the receiving portions 310 can be smaller to minimize the chance of error in coupling the ring 1702 with the tubular structure 12.

Figure 17C:
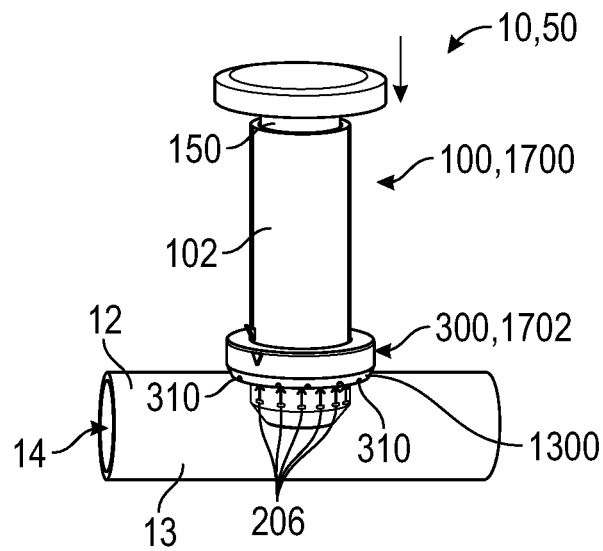
FIG. 17C illustrates actuation of the fixation device.

As illustrated in FIG. 17A-17C, the ring 1702 can be positioned opposite the cartridge 1710 in relation to the wall 13 of the tubular structure 12. The ring 1702 can be positioned external of the tubular structure 12 so that the ring 1702 does not cause any obstruction in the lumen 14 of the tubular structure 12. The cartridge 1710, as illustrated in FIGS. 17A-17C, can be positioned inside the lumen 14 of the tubular structure 12 to push the fasteners 260 across the wall 13 of the tubular structure 12 into the receiving portions 310 of the ring 1702. In some examples, the cartridge 1710 may also be positioned external of the tubular structure 12, so long as the fasteners 260 can couple the ring 1702 with the tubular structure 12.

As illustrated in FIG. 17C, the fixation device 1700 can be actuated so that the plurality of fasteners 260 puncture the tubular structure 12 and are received by the receiving portions 310. Accordingly, the tubular structure 12 can be coupled with the ring 1702. In at least one example, as illustrated in FIG. 17C, the fixation device 1700 can include a pusher rod 150. Upon actuation of the fixation device 1700, the pusher rod 150 can translate along a longitudinal axis to activate drivers to push the corresponding fasteners 260 from the cartridge 1710. In some examples, the fixation device 1700 can have any suitable mechanism to activate the drivers to push the fasteners 260 from the cartridge 1710.

Figure 17D:
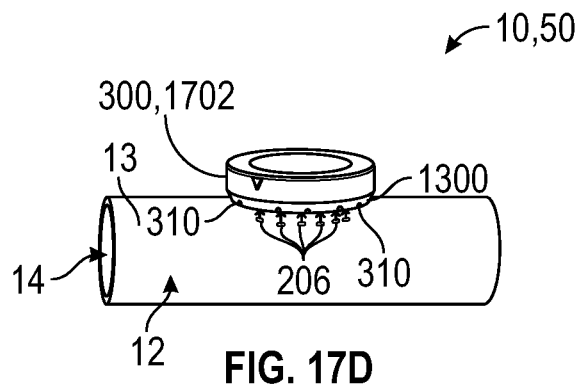
FIG. 17D illustrates the ring being coupled with the side of the tubular structure.

As illustrated in FIG. 17D, after the ring 1702 is coupled with the tubular structure 12, the fixation device 1700, along with the cartridge 1710, can be removed. The ring 1702 remains coupled with the tubular structure 12 such that the aperture 302 of the ring 1702 is aligned with the hole 1300 in the wall 13 of the tubular structure 12.

Figure 17E:
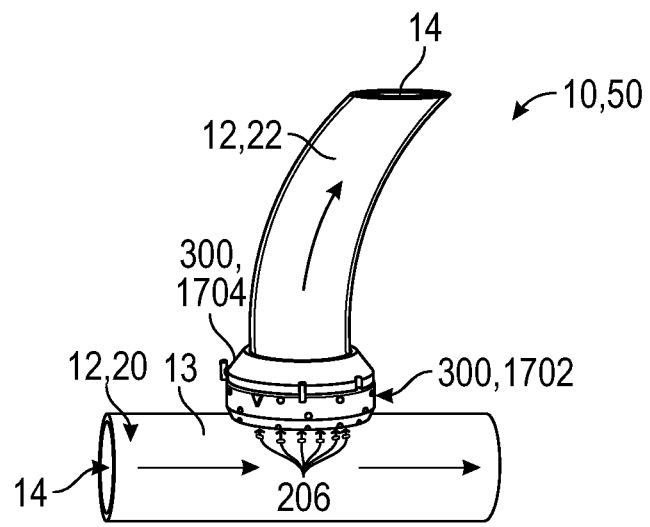
FIG. 17E illustrates a second tubular structure being coupled with the tubular structure.

As illustrated in FIG. 17E, the ring 1702 is operable to be coupled with a second tubular structure 22 such that a lumen 14 of the second tubular structure 22 is in fluid communication with the lumen 14 of the tubular structure 20 via the hole 1300 formed in the wall 13 of the tubular structure 20. The side ring 1702 is operable to be coupled with the first tubular structure 20 such that the aperture 302 of the side ring 1702 is aligned with the hole 1300 formed in the wall 13 of the first tubular structure 12. The end ring 1704, similar to the rings 350, 360 as illustrated in FIGS. 1-14, is operable to be coupled with a second tubular structure 22 such that the aperture 302 of the end ring 1704 is in line with the lumen 14 of the second tubular structure 22. The side ring 1702 is operable to be coupled with the end ring 1704 such that the lumen 14 of the second tubular structure 22 is in fluid communication with the lumen 14 of the first tubular structure 20 via the hole 1300 formed in the wall 13 of the first tubular structure 20. Accordingly, an end-to-side anastomosis is achieved. In some examples, the side ring 1702 and the end ring 1704 create a seal to prevent fluid leakage. The seal can be achieved by any suitable mechanism.

As illustrated in FIG. 17E, fluid may flow through the lumen 14 of the first tubular structure 20 while some fluid may flow into and through the lumen 14 of the second tubular structure 22. In some examples, fluid from the second tubular structure 22 may flow into the first tubular structure 20.

The aforementioned side-to-end anastomotic coupler 50 and system provides users with a better, more reliable alternative to the conventional techniques. The only technique conventionally practiced for side-to-end anastomosis is through hand-sewn suture techniques. Hand-sewn suture techniques are labor intensive and prone to failure. Similarly, the process of creating the side opening in the tubular structure is conventionally completed in an uncontrolled fashion using a scalpel or scissors to haphazardly cut the side of the structure, which can result in an asymmetric opening of variable size.

Referring to FIG. 18, a flowchart is presented in accordance with an example embodiment. The method 1800 is provided by way of example, as there are a variety of ways to carry out the method. The method 1800 described below can be carried out using the configurations illustrated in FIG. 1-17E, for example, and various elements of these figures are referenced in explaining example method 1800. Each block shown in FIG. 18 represents one or more processes, methods or subroutines, carried out in the example method 1800. Furthermore, the illustrated order of blocks is illustrative only and the order of the blocks can change according to the present disclosure. Additional blocks may be added or fewer blocks may be utilized, without departing from this disclosure. The example method 1800 can begin at block 1802.

At block 1802, a side ring is coupled with a first tubular structure such that an aperture of the side ring is aligned with a hole formed in a wall of the first tubular structure.

At block 1804, the side ring is coupled with a second tubular structure such that a lumen of the second tubular structure is in fluid communication with a lumen of the first tubular structure via the hole formed in the wall of the first tubular structure. In at least one example, the second tubular structure can be coupled with an end ring such that an aperture of the end ring is in line with the lumen of the second tubular structure. The side ring can be coupled with the end ring to join the first tubular structure with the second tubular structure. In at least one example, the side ring and the end ring can create a seal to prevent fluid leakage.

FIGS. 19-25C illustrate examples of an anastomotic coupler 10 which is operable to couple two tubular structures 12 with a cartridge 200 having fasteners 206 extending therefrom at an angle 1902A. Elements described in the system of FIGS. 19-25C that have similar or the same name and/or the same reference numbers as elements in the disclosure for FIGS. 1-18 may have the same features and/or functions as discussed above. While the discussion below for FIGS. 19-25C may highlight some differences in features, the disclosure for the system of FIGS. 19-25C are not limited to those and may also include any and/or all of the features as discussed above. Similarly, the examples in FIGS. 1-18 may utilize any and/or all of the features as discussed below for FIGS. 19-25C.

FIG. 19 illustrates an exemplary cartridge 200, 1900 which includes a body 1901 and fasteners 206, 1902 extending from the body 1901. The body 1901, as illustrated in FIG. 19, can be substantially cylindrical. In other examples, the body 1901 can be in other configurations or shapes such as rectangular, ovoid, or any other suitable shape. In some examples, the body 1901 can include mesh, braided mesh, stent, and may be a solid ring and/or tube, and/or any combination of mesh, stent, and solid material. The body 1901 can form a lumen 1903 which passes through the body 1901. The lumen 1903 is operable to permit fluidic passage across the body 1901 through the lumen 1903. Accordingly, when the cartridge 1900 is disposed within the tubular structure(s) 12, the lumen 1903 is in fluid communication with the lumen 14 of the tubular structure(s) 12 such that fluid can pass through the lumen 1903 between the tubular structure(s) 12.

The fasteners 1902 extend from the body 1901 of the cartridge 1900 at an angle 1902A from the body 1901. For example, the fasteners 1902 may extend at an angle 1902A that is between about 1 degree and about 89 degrees. The fasteners 1902 may extend at an angle 1902 that is greater than 0 degrees and less than 90 degrees. In such an example, the fasteners 1902 may be deployed by rotating the fasteners 1902 in relation to the tubular structure 12. In some examples, the fasteners 1902 may extend at an angle 1902A of 90 degrees (directly radially outward similar to FIGS. 1-18), and may be actuated by expansion of the body 1901 of the cartridge 200. The fasteners 1902 are operable to puncture through a wall of one and/or two tubular structure(s) 12. In some examples, the fasteners 1902 can have a hook design.

In at least one example, as illustrated in FIG. 19, the fasteners 1902 can be coupled to the body 1901 of the cartridge 1900. In some examples, as illustrated in FIGS. 22A-25C, the fasteners 1902 can be formed as a part of the body 1901 such that the fasteners 1902 and the body 1901 are one unitary piece and/or material.

FIG. 20 illustrates a sheath 2000 operable to cover the fasteners 1902. Accordingly, upon insertion of the cartridge 1900 into the tubular structure 12, the fasteners 1902 are not inadvertently scratching and/or puncturing the tubular structure 12.

As the fasteners 1902 extend at an angle 1902A from the body 1901, the fasteners 1902 are operable to puncture through the tubular structure 12 when the cartridge 1900 is rotated about a longitudinal axis in relation to the tubular structure 12. Due to the fasteners 1902 puncturing the tubular structure 12 at an angle, the fasteners 1902 couple the cartridge 1900 with the tubular structure 12 so that the fasteners 1902 are not easily removed. For example, the tubular structure 12 or the cartridge 1900 would have to move relative to one another at a specification rotation and distance from one another to de-couple the fasteners 1902 from the tubular structure 1900.

Figure 21A:
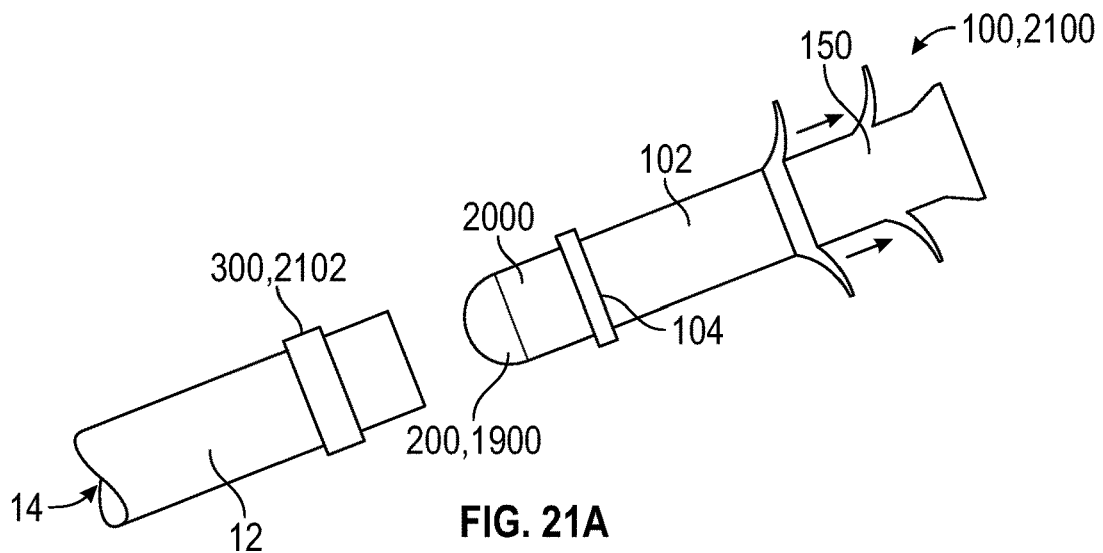
FIGS. 21A, 21B, and 21C illustrate actuation of a fixation device.
Figure 21B:
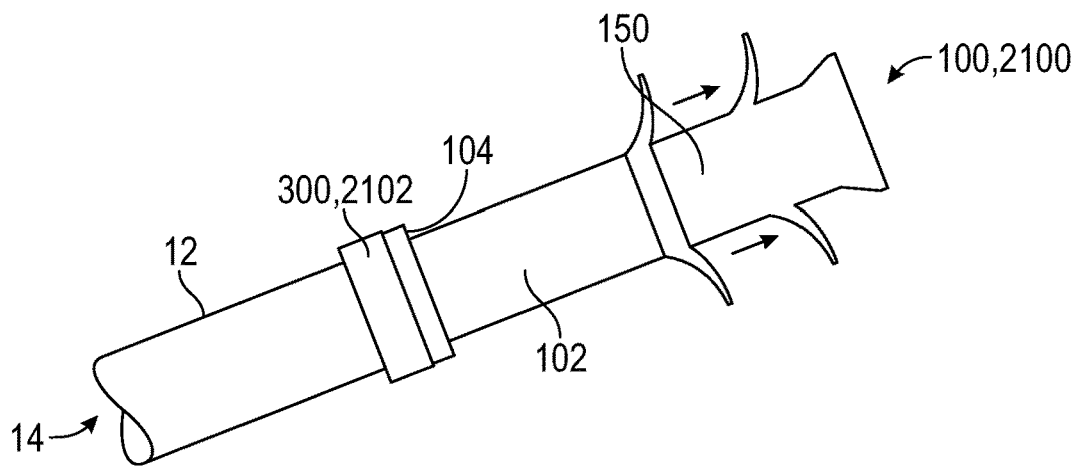
Figure 21C:
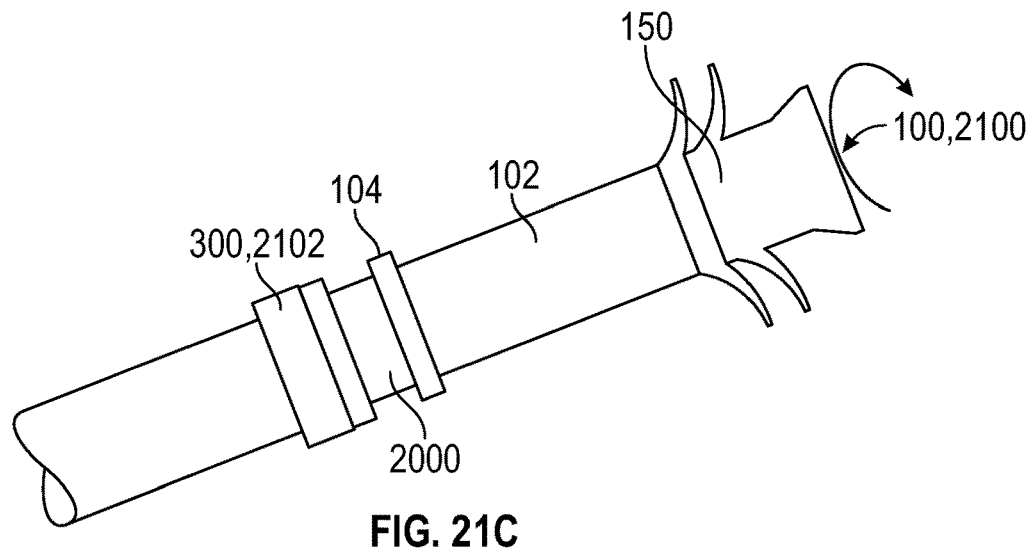

FIGS. 21A-21C illustrate an example of actuation of the cartridge 1900 to couple the cartridge 1900 with a tubular structure 12. The anastomotic coupler 10, in the example illustrated in FIGS. 21A-21C, can include a fixation device 100, 2100. The fixation device 100, 2100 can be similar to the fixation device 100 described above for FIGS. 1-18. A ring 300, 2102 can be provided about the tubular structure 12, external the annulus 14. The fixation device 2100 includes a housing 102 and an actuation mechanism 150, for example a pusher rod, a button, a motor, and/or any other suitable mechanism to actuate the cartridge 1900. The cartridge 1900 can be coupled with the fixation device 2100. A stop 104 can be positioned on the housing 102 adjacent to the cartridge 1900. As shown in FIG. 21B, the stop 104 is operable to abut against the edge of a tubular structure 12 to ensure accurate positioning of the cartridge 1900 within the annulus 14 of the tubular structure 12. As illustrated in FIG. 21B, the cartridge 1900 is inserted into the annulus 14 of the tubular structure 12. In at least one example, the ring 2102 can abut the stop 104 to accurately position the ring 2102 to be aligned with the cartridge 1900.

While the examples illustrated in FIGS. 21A-25C illustrate the cartridge 1900 being disposed within the annulus 14 and the ring 2102 disposed external the tubular structure 12, in other examples the cartridge 1900 can be disposed external the tubular structure 12 while the ring 2102 is disposed within the annulus 14.

As shown in FIG. 21B, the actuation mechanism 150 can be actuated, for example pulled away from the housing 102, to move the sheath 2000 to expose the fasteners 1902. Other mechanisms to remove the sheath 2000 to expose the fasteners 1902 can be utilized, for example pulling a string, cutting apart the sheath 2000, or any other suitable mechanism to expose the fasteners 1902 of the cartridge 1900 after the cartridge 1900 has been disposed within the annulus 104 of the tubular structure 102.

As illustrated in FIG. 21C, the actuation mechanism 150 can be actuated, for example rotated or push a button or any other suitable mechanism, to rotate the cartridge 1900 and puncture the tubular structure 12 with the fasteners 1902. The fasteners 1902 are operable to be rotated to engage the tubular structure 12, as the fasteners 1902 extend at the angle 1902A from the body 1901 of the cartridge 1900.

In some examples, the cartridge 1900 can also expand radially to push the body 1901 of the cartridge 1900 and subsequently the fasteners 1902 against the tubular structure 12. In some examples, the body 1901 of the cartridge 1900 and/or the fasteners 1902 can expand radially by expansion, rotation, balloon expansion, traction, compression, and/or any other suitable mechanism. By pushing the fasteners 1902 against the tubular structure 12, the fasteners 1902 may puncture the tubular structure 12. In some examples, the cartridge 1900 and/or the fasteners 1902 can be rotated after puncturing the tubular structure 12 to secure the coupling of the cartridge 1900 with the tubular structure 12.

The fasteners 1902 are then secured by and/or in the ring 2102 to maintain the position and coupling of the cartridge 1900 with the tubular structure 12. Examples of the mechanism to retain the fasteners 1902 in the ring 2102 and/or configurations of the cartridge 1900 are illustrated in FIGS. 22A-25C. FIGS. 22A-25C illustrate different mechanisms of utilizing gaskets 2200 as receiving portions for the fasteners 1902.

Figure 22A:
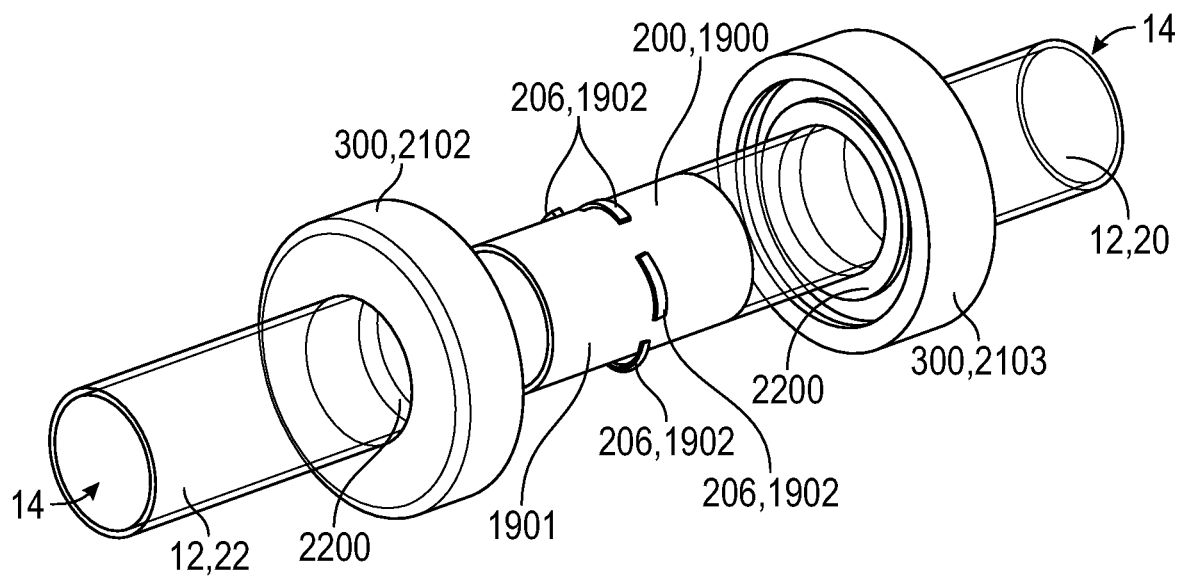
FIGS. 22A, 22B, and 22C illustrate coupling two tubular structures with an exemplary cartridge.
Figure 22B:
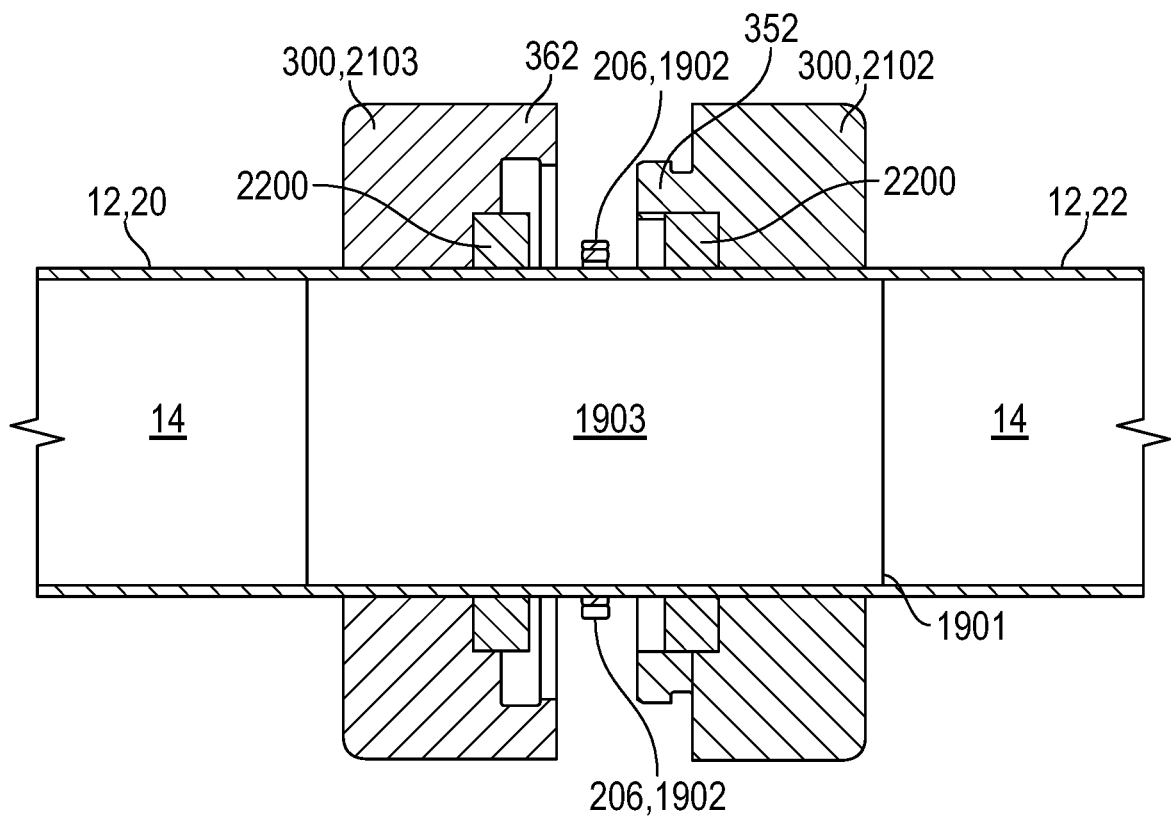
Figure 22C:
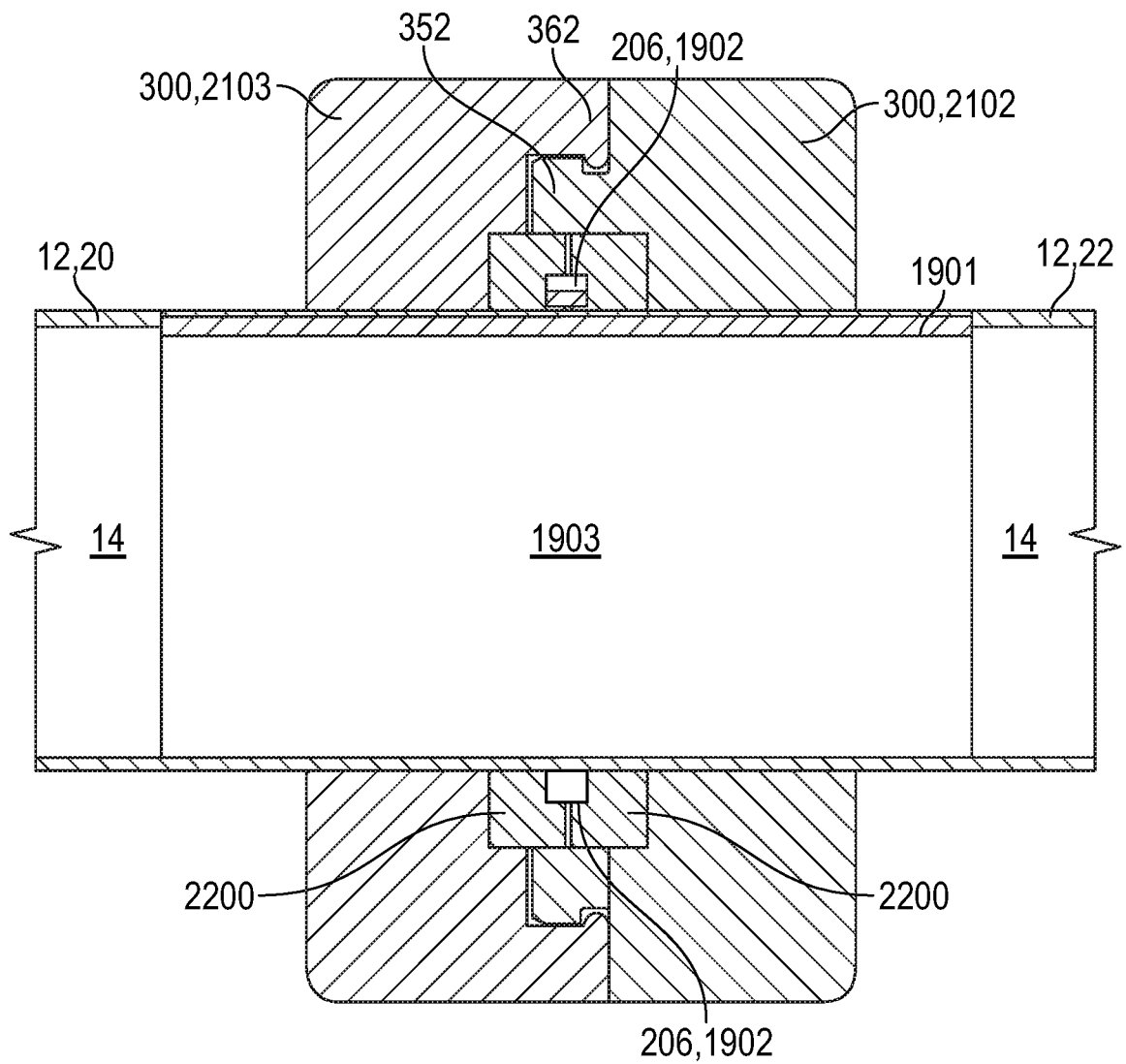

FIGS. 22A-22C illustrate an example of a cartridge 1900 that has one row of fasteners 1902 and rings 300 that secure the fasteners 1902 by compression between two gaskets 2200. To secure two tubular structures 20, 22 to the cartridge 1900, the two tubular structures 20, 22 may overlay one another over the fasteners 1902 of the cartridge 1900. The fasteners 1902 may puncture the two tubular structures 20, 22 to secure the cartridge 1900 against the two tubular structures 20, 22 and align the lumen 14 of each of the tubular structures 20, 22 and the lumen 1903 of the cartridge 1900. Accordingly, fluid can pass through a tubular structure 20, through the cartridge 1900, and to the other tubular structure 22.

As illustrated in FIGS. 22B-22C, the two rings 2102, 2103 can be brought together to couple with one another via mating portions 352, 362 (similar to FIGS. 1-18). Upon coupling of the mating portions 352, 362, gaskets 2200 for each of the rings 2102, 2103 compress against each other, receiving the fasteners 1902 between the two gaskets 2200. In some examples, the compression of the gaskets 2200 against the fasteners 1902 can sufficiently secure the coupling of the rings 2102, 2103 with the cartridge 1900. In some examples, after compression of the gaskets 2200 against the fasteners 1902, the fasteners 1902, the rings 2102, 2103, and/or the gaskets 2200 may be rotated so that the fasteners 1902 puncture into the gaskets 2200. In some examples, the fasteners 1902 may be received by the gaskets 2200 or the ring 2102, 2103. In some examples, the gaskets 2200 can be made of any biocompatible material including silicone, rubber, and other elastomers, including thermoplastic and/or bioresorbable elastomers. In some examples, the gaskets 2200 can be made of polyurethane elastomer, polydiene, poly(vinyl) chloride elastomers, and/or any other suitable material.

Figure 23A:
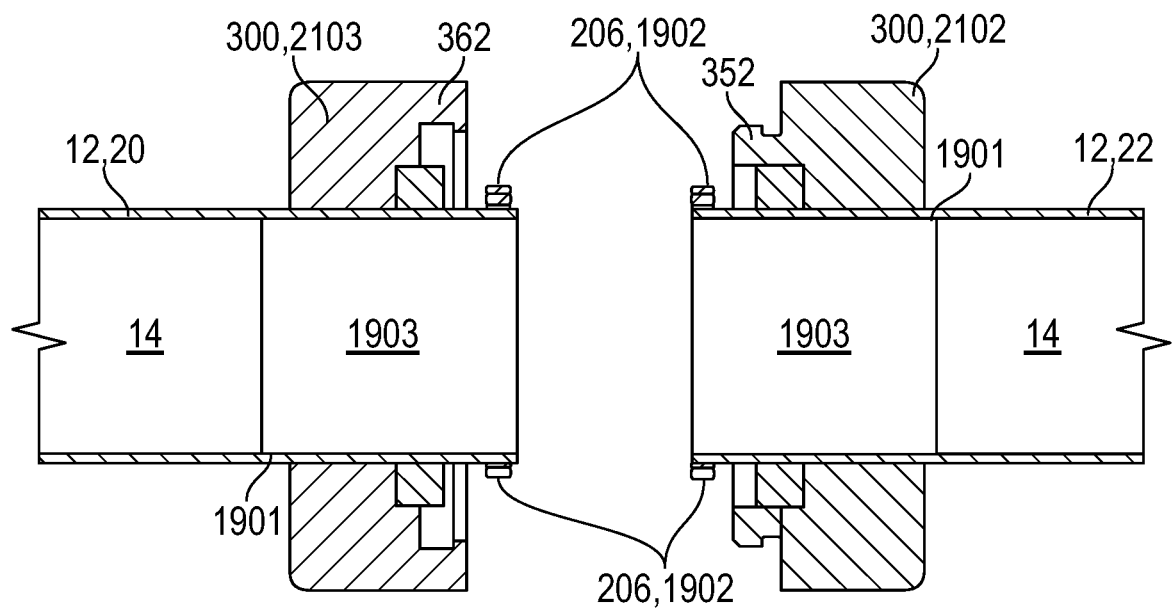
FIGS. 23A, 23B, and 23C illustrate coupling two tubular structures with an exemplary cartridge.
Figure 23B:
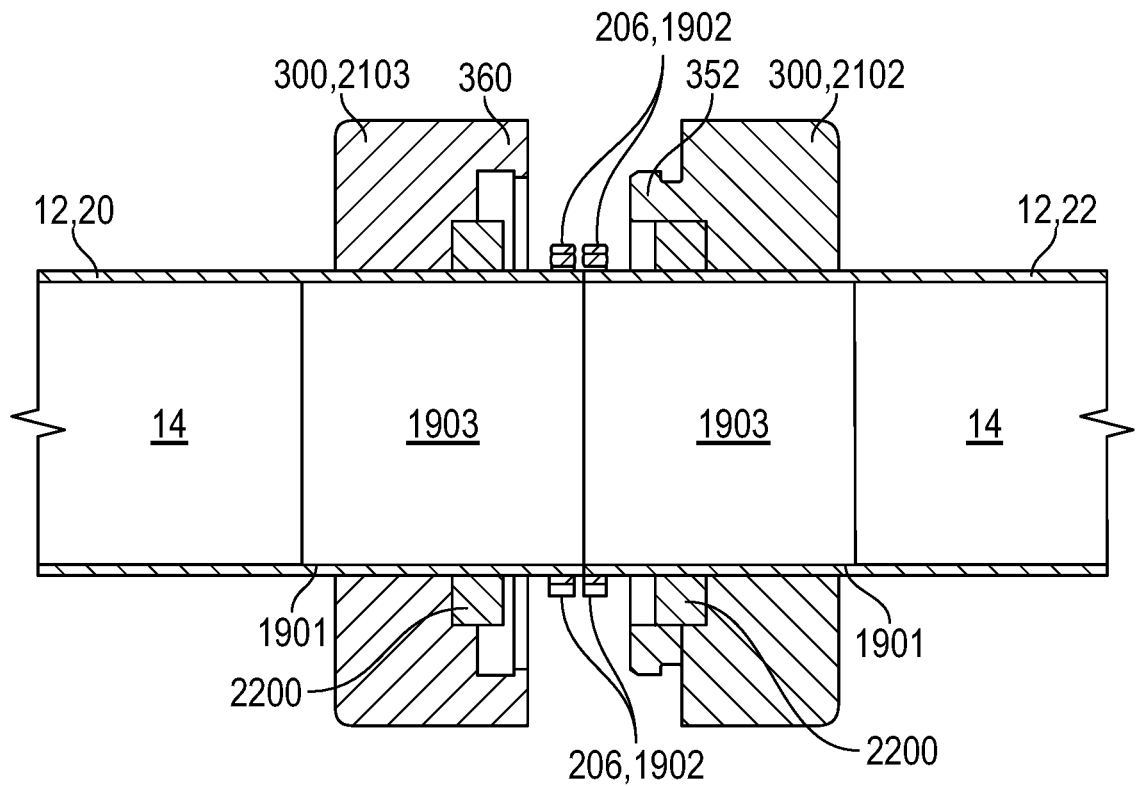
Figure 23C:
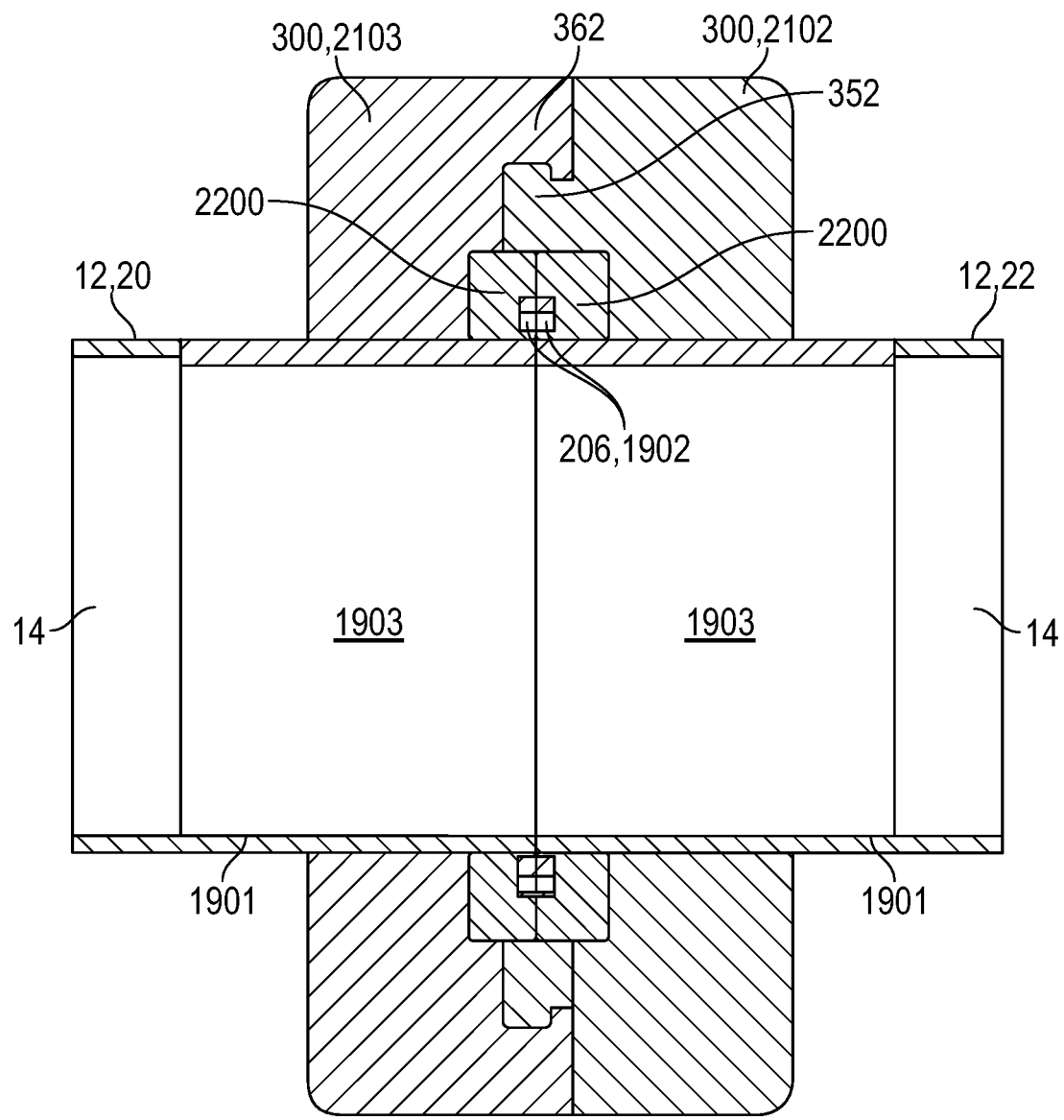

FIGS. 23A-23C illustrate an example of utilizing two separate cartridges 1900 coupled with a corresponding tubular structure 20, 22, and securing the fasteners 1902 by compression between the two gaskets 2200. As illustrated in FIGS. 23A-23C, each of the cartridges 1900 can include at least one row of fasteners 1902. Each of the fasteners 1902 have punctured the corresponding tubular structures 20, 22. The two tubular structures 20, 22, each with cartridges 1900 coupled thereto, are brought together so that the lumens 14 are in fluid communication with one another through the lumens 1903 of the cartridges 1900. Similar to FIGS. 22A-22C, the rings 2102, 2103 are brought together and coupled with one another via mating portions 352, 362. Upon bringing the rings 2102, 2103 together, gaskets 2200 for each of the rings 2102, 2103 compress against each other, receiving the fasteners 1902 for the two cartridges 1900 between the two gaskets 2200. In some examples, the compression of the gaskets 2200 against the fasteners 1902 can sufficiently secure the coupling of the rings 2102, 2103 with the cartridges 1900. In some examples, after compression of the gaskets 2200 against the fasteners 1902, the fasteners 1902, the rings 2102, 2103, and/or the gaskets 2200 may be rotated so that the fasteners 1902 puncture into the gaskets 2200. In some examples, the fasteners 1902 may be received by the gaskets 2200 or the ring 2102, 2103.

Figure 24A:
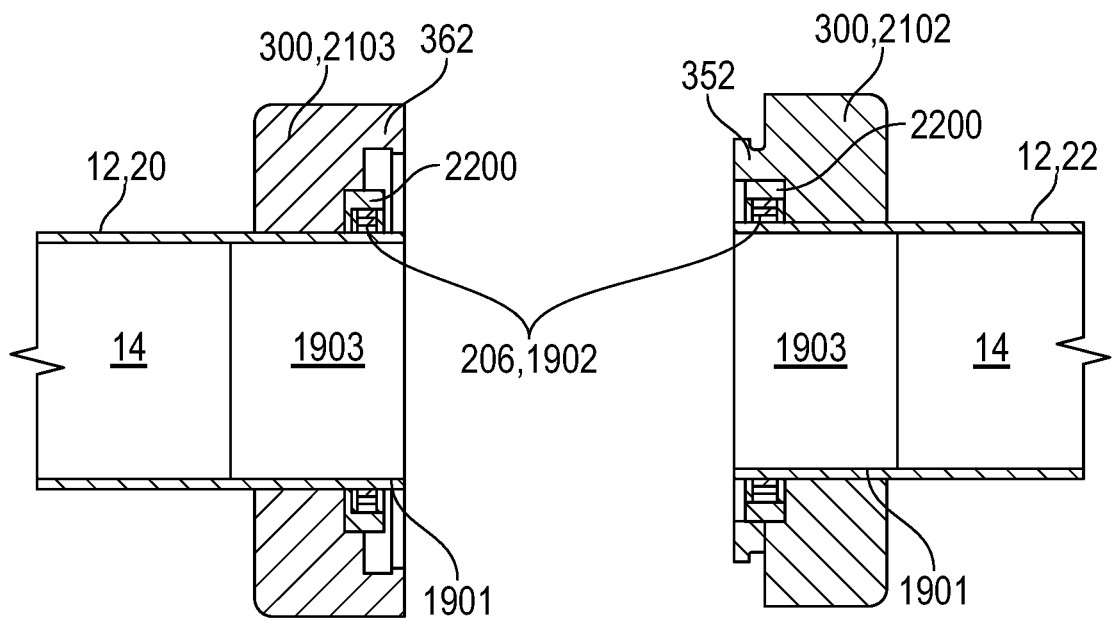
FIGS. 24A, 24B, and 24C illustrate coupling two tubular structures with an exemplary cartridge.
Figure 24B:
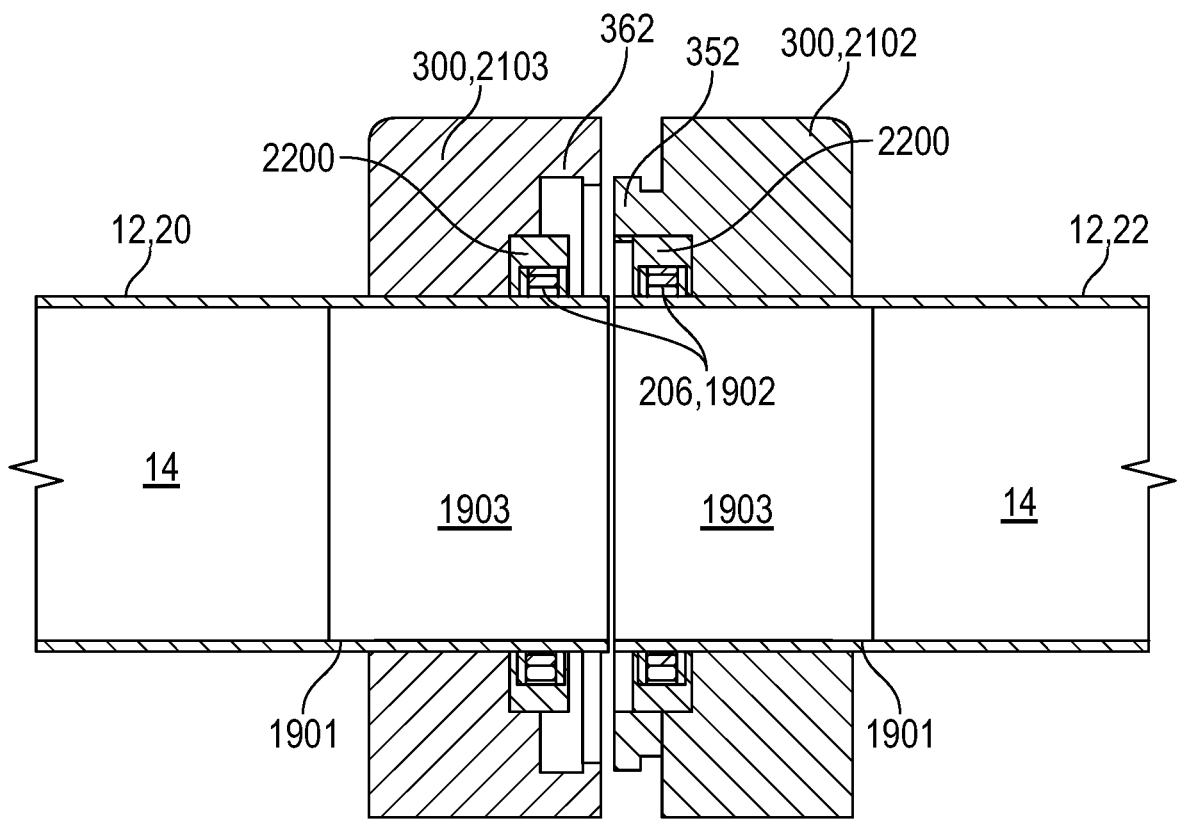
Figure 24C:
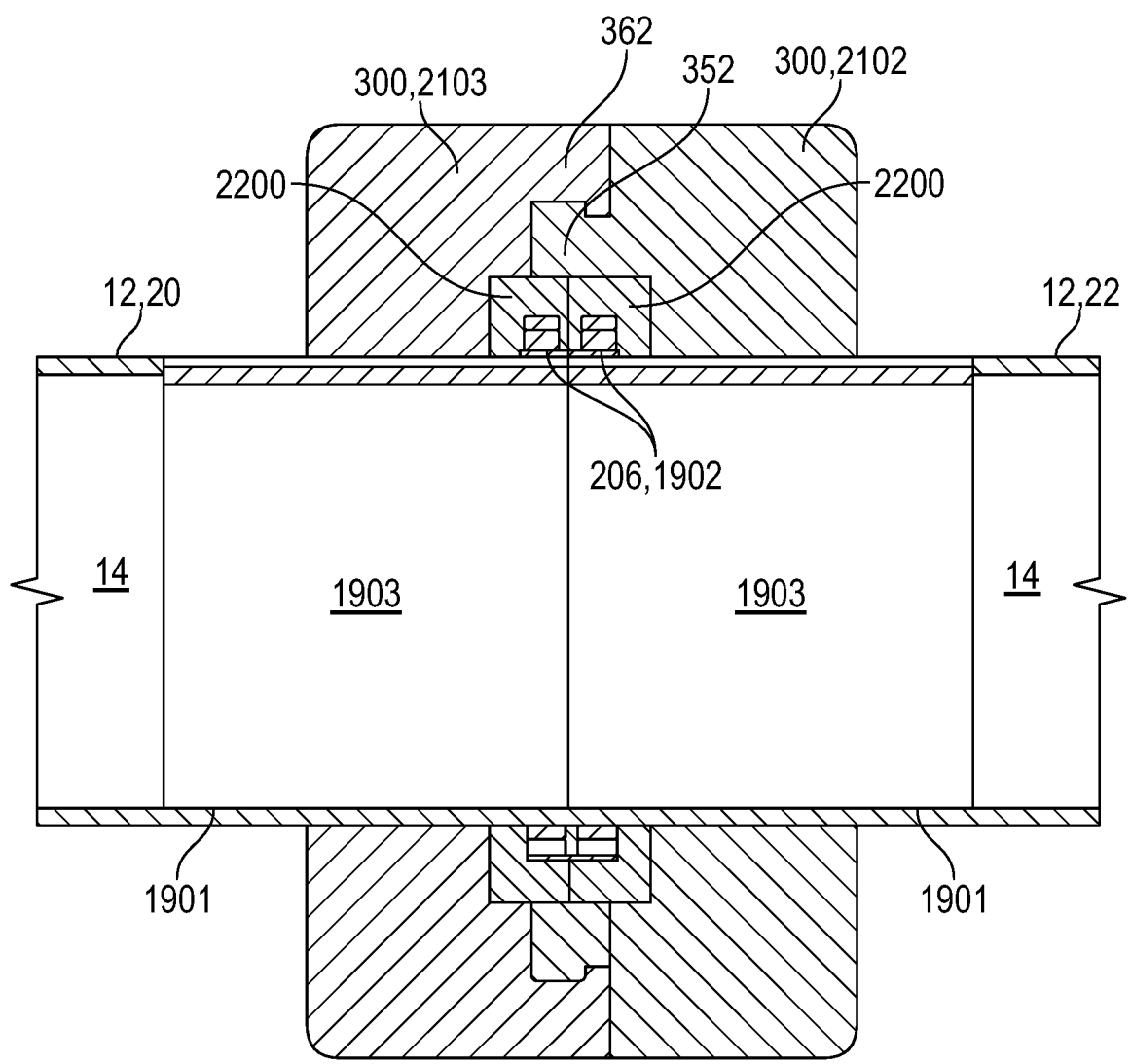

FIGS. 24A-24C illustrate an example of the fasteners 1902 directly puncturing into the gasket 2200 of the corresponding ring 300 while puncturing through the tubular structure 12. The rings 2102, 2103 are then brought together and coupled with one another via mating portions 352, 362. While FIGS. 24A-24C illustrate an example similar to FIGS. 23A-23C where two separate cartridges 1900 are utilized, in some examples, similar to FIGS. 22A-22C, one cartridge 1900 may be utilized. FIGS. 24A-24C illustrate the mechanism of the fasteners 1902 being directly received in and/or puncturing the corresponding gasket 2200. This mechanism can be utilized in addition to and/or in place of compressing the fasteners 1902 with the gaskets 2200.

Figure 25A:
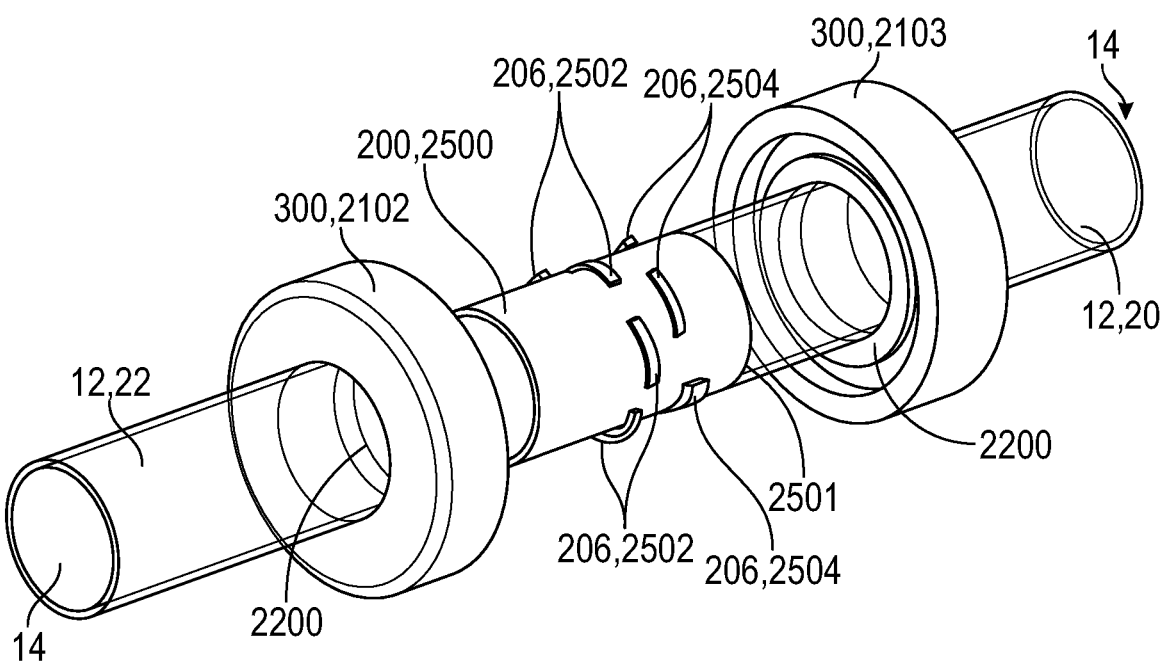
FIGS. 25A, 25B, and 25C illustrate coupling two tubular structures with an exemplary cartridge.
Figure 25B:
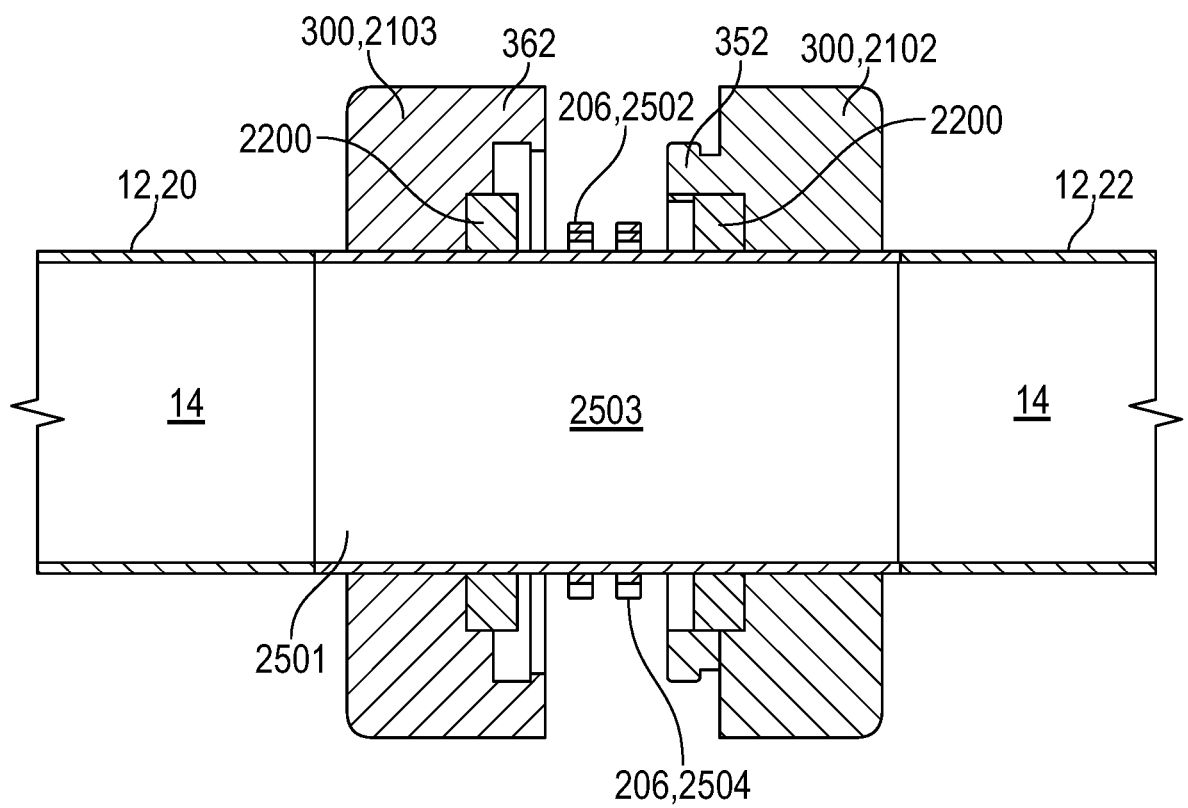
Figure 25C:
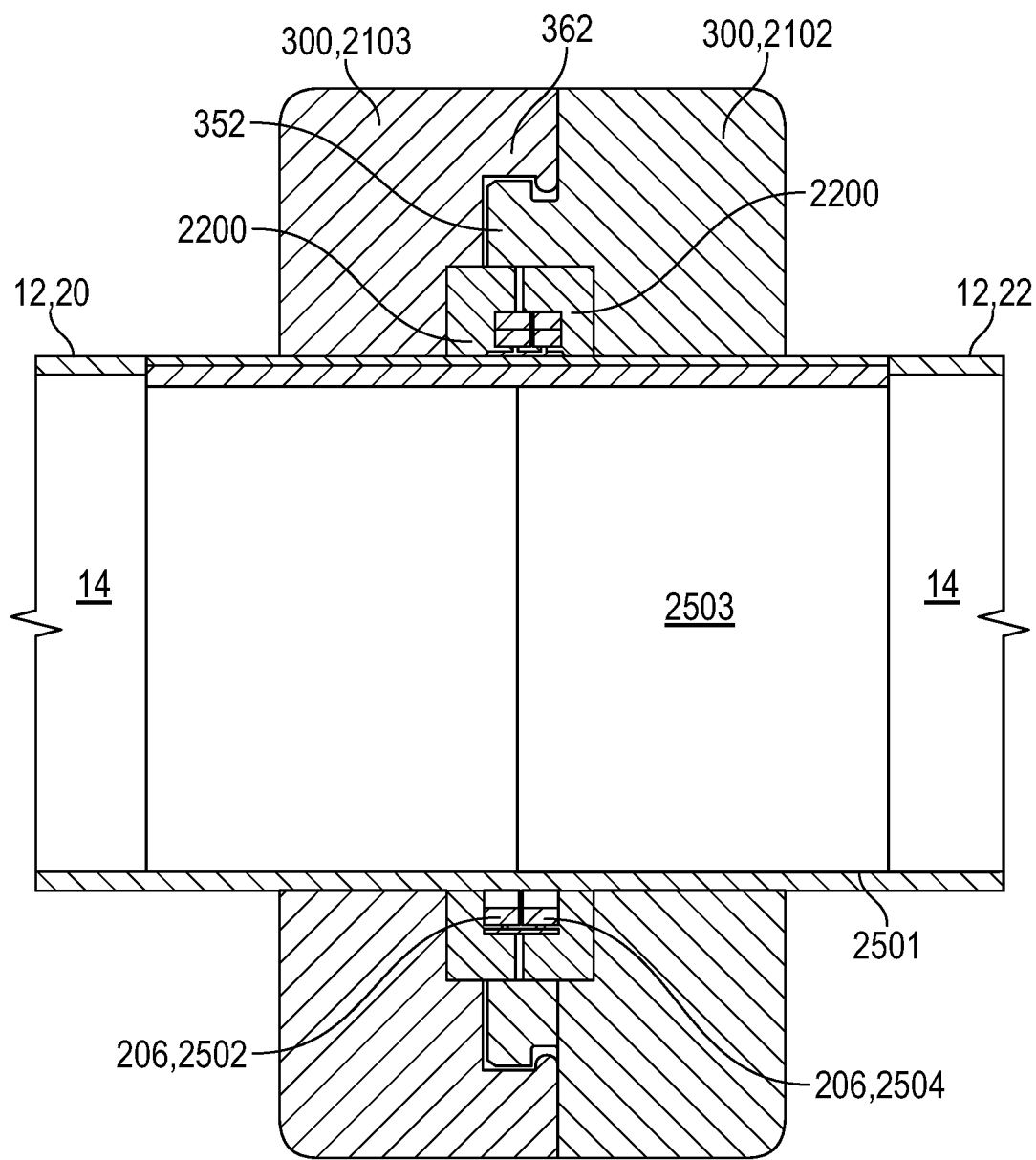

FIGS. 25A-25C illustrate an example of a cartridge 1900 that includes two (or more) rows of fasteners 1902 on one body 1901. Accordingly, instead of overlaying the two tubular structures 20, 22 as in FIGS. 22A-22C, each tubular structure 20, 22 may couple with a corresponding row of fasteners 1902. In some examples, even with multiple rows of fasteners 1902, the tubular structures 20, 22 may still overlap over one or more rows of fasteners 1902. The rings 2102, 2103 are brought together and coupled with one another via mating portions 352, 362. Upon bringing the rings 2102, 2103 together, gaskets 2200 for each of the rings 2102, 2103 compress against each other, receiving the fasteners 1902 for the two cartridges 1900 between the two gaskets 2200. In some examples, the compression of the gaskets 2200 against the fasteners 1902 can sufficiently secure the coupling of the rings 2102, 2103 with the cartridges 1900. In some examples, after compression of the gaskets 2200 against the fasteners 1902, the fasteners 1902, the rings 2102, 2103, and/or the gaskets 2200 may be rotated so that the fasteners 1902 puncture into the gaskets 2200.

The disclosures shown and described above are only examples. Even though numerous properties and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

The invention claimed is:

1. An anastomotic coupler comprising:
   a ring;
   a cartridge including a body and a plurality of fasteners extending from the body at an angle,
   wherein the ring is aligned with the cartridge in that the cartridge is disposed within a lumen of a tubular structure and the ring is positioned external of the tubular structure,
   wherein the plurality of fasteners are operable to puncture the tubular structure,
   wherein the plurality of fasteners are operable to be received by the ring such that the tubular structure is coupled with the ring.

2. The anastomotic coupler of claim 1, wherein a fixation device includes a stop, the stop extending radially from a housing such that a free end of the tubular structure abuts the stop.

3. The anastomotic coupler of claim 1, wherein upon actuation of a fixation device, the fasteners rotate in relation to the tubular structure.

4. The anastomotic coupler of claim 1, wherein a sheath is provided to cover the fasteners until the cartridge is positioned inside the tubular structure.

5. The anastomotic coupler of claim 4, wherein the sheath is removed to uncover the fasteners after the cartridge is positioned inside the tubular structure.

6. The anastomotic coupler of claim 1, wherein upon actuation of a fixation device, the body of the cartridge expands radially against the tubular structure.

7. The anastomotic coupler of claim 1, wherein the angle of the fasteners in relation to the body is greater than 0 degrees and less than 90 degrees.

8. The anastomotic coupler of claim 1, wherein one row of fasteners is provided on the cartridge.

9. The anastomotic coupler of claim 1, wherein two rows of fasteners are provided on the cartridge.

10. The anastomotic coupler of claim 1, wherein the ring includes a receiving portion, the receiving portion includes one or more gaskets.

11. The anastomotic coupler of claim 10, wherein at least one of the fasteners are operable to directly puncture the one or more gaskets upon puncturing the tubular structure.

12. The anastomotic coupler of claim 11, wherein the at least one of the fasteners are compressed between two gaskets of the one or more gaskets.

* * * * *